(12) United States Patent
Ikebe

(10) Patent No.: US 12,039,888 B2
(45) Date of Patent: Jul. 16, 2024

(54) EDUCATIONAL ELECTRONIC HEALTH RECORD SYSTEM AND EDUCATIONAL ELECTRONIC HEALTH RECORD PROGRAM

(71) Applicant: Medi-LX Inc., Osaka (JP)

(72) Inventor: Ryo Ikebe, Izumi (JP)

(73) Assignee: MEDI-LX INC., Osaka (JP)

(*) Notice: Subject to any disclaimer, the term of this patent is extended or adjusted under 35 U.S.C. 154(b) by 0 days.

(21) Appl. No.: 18/015,604

(22) PCT Filed: Oct. 4, 2021

(86) PCT No.: PCT/JP2021/036633
§ 371 (c)(1),
(2) Date: Jan. 11, 2023

(87) PCT Pub. No.: WO2022/190442
PCT Pub. Date: Sep. 15, 2022

(65) Prior Publication Data
US 2023/0252904 A1 Aug. 10, 2023

(30) Foreign Application Priority Data
Mar. 12, 2021 (JP) .................. 2021-040537

(51) Int. Cl.
*G09B 5/02* (2006.01)
*G16H 10/60* (2018.01)

(52) U.S. Cl.
CPC .............. *G09B 5/02* (2013.01); *G16H 10/60* (2018.01)

(58) Field of Classification Search
CPC .................................. G09B 5/02; G16H 10/60
See application file for complete search history.

(56) References Cited

U.S. PATENT DOCUMENTS

2010/0287472 A1* 11/2010 Eversole .................. G06F 8/61
715/705
2015/0154361 A1* 6/2015 Barsoum ................ G16H 10/60
705/3

(Continued)

FOREIGN PATENT DOCUMENTS

| JP | 2015-219247 A | 12/2015 |
| JP | 2018-124979 A | 8/2018 |
| JP | 2019-191727 A | 10/2019 |

OTHER PUBLICATIONS

Uno Fumio et al., "Developmetn of an Electronic Medical Record Education Sytem as a New Basic Nursing Educational Media" The bulletin of Niimi college, Dec. 25, 2009, vol. 30, pp. 37-44; cited in the ISR and JP Office Action dated Dec. 13, 2021; w/machine translation.

(Continued)

*Primary Examiner* — Eddy Saint-Vil
(74) *Attorney, Agent, or Firm* — WHDA, LLP

(57) ABSTRACT

Provided are an educational electronic health record system and an educational electronic health record program that enable the use of patient health record information having an information amount greater than or equal to that of an electronic health record used in the actual medical setting by responding to various needs of a learner or advanced and complicated medical information, and thus, enable effective education and training for the learner such as a medical service worker. An educational electronic health record system of the present invention includes at least an educational electronic health record server 10 that includes a data file acquisition unit 112 acquiring a data file that is described in a data format of arbitrary software and includes simulated patient information, a storage unit 102 storing the simulated patient information of the data file acquired by the data file acquisition unit 112, and a patient health record information (Continued)

generation unit 113 calling the simulated patient information from the storage unit 102 and generating patient health record information displayed on a learner terminal 40, based on the simulated patient information.

6 Claims, 27 Drawing Sheets

(56) References Cited

U.S. PATENT DOCUMENTS

| | | | | |
|---|---|---|---|---|
| 2020/0118691 | A1* | 4/2020 | Kiljanek | G16H 50/20 |
| 2020/0365273 | A1* | 11/2020 | Mitsumori | G16H 50/20 |
| 2021/0290077 | A1* | 9/2021 | Lee | G16H 10/60 |

OTHER PUBLICATIONS

International Search Report dated Dec. 14, 2021, issued in counterpart International Application No. PCT/JP2021/036633.
Office Action dated Dec. 13, 2021, issued in counterpart JP Application No. 2021-163078; w/machine translation.
Notice of Reasons for Revocation dated Mar. 28, 2023, issued in counterpart JP application No. 2021-163078, with English translation. (112 pages).
Exhibit No. 1-Medi-EYE User's Guide ver. 1.9 <https://medi-lx.co.jp/images/upload_file/Medi-EYE%E3%83%A6%E3%83%BC%E3%82%B5%E3%82%99%E3%83%BC%E3%82%B9%E3%82%99%E3%82%AB%E3%82%99%E3%82%A4%E3%83%88%E3%82%99%20ver.1.9.pdf>; w/Machine Translation; Cited in Written Opposition dated Jan. 27, 2023.
Exhibit No. 5-1-Output Document of <https://medi-lx.co.jp/site/login>; w/Machine Translation; Cited in Written Opposition dated Jan. 27, 2023.
Exhibit No. 5-2-Output Document of Whole Information Text of <https://medi-lx.co.jp/site/login>; w/Partial Machine Translation; Cited in Written Opposition dated Jan. 27, 2023.
Exhibit No. 5-3-Output Document of Source Cord of <https://medi-lx.co.jp/site/login>; Cited in Written Opposition dated Jan. 27, 2023.
Exhibit No. 6-1-Output Document of https://web.archive.org/web/20220000000000 *https://medi-lx.co.jp/site/login showing archive record of <https://medi-lx.co.jp/site/login>; Cited in Written Opposition dated Jan. 27, 2023.
Exhibit No. 6-2-Output Document of https://web.archive.org/web/20220405234345/ https://medi-lx.co.jp/site/login which is archive record of <https://medi-lx.co.jp/site/login> archived on Apr. 5, 2022; w/Machine Translation; Cited in Written Opposition dated Jan. 27, 2023.
Exhibit No. 6-3-Output Document of Whole Information Text of https://web.archive.org/web/20220405234345/https://medi-lx.co.jp/site/login which is archive record of <https://medi-lx.co.jp/site/login>; w/Partial Machine Translation; Cited in Written Opposition dated Jan. 27, 2023.
Exhibit No. 6-4-Output Document of Source Cord of https://web.archive.org/web/20220405234345/ https://medi-lx.co.jp/site/login which is archive record of <https://medi-lx.co.jp/site/login>; Cited in Written Opposition dated Jan. 27, 2023.
Exhibit No. 7-0-Medi-EYE User's Guide ver. 1.0; w/Machine Translation; Cited in Written Opposition dated Jan. 27, 2023.
Exhibit No. 7-1-Medi-EYE User's Guide ver. 1.1; w/Machine Translation; Cited in Written Opposition dated Jan. 27, 2023.
Exhibit No. 7-2-Medi-EYE User's Guide ver. 1.2; w/Machine Translation; Cited in Written Opposition dated Jan. 27, 2023.
Exhibit No. 7-3-Medi-EYE User's Guide ver. 1.3; w/Machine Translation; Cited in Written Opposition dated Jan. 27, 2023.
Exhibit No. 7-4-Medi-EYE User's Guide ver. 1.4; <https://medi-lx.jp/images/upload/Medi-EYE%E3%83%A6%E3%83%BC%E3%82%B5%E3%8 2%99%E3%83%BC%E3%82%B9%E3%82%99; %E3%82%AB%E3%82%99%E3%82%A4%E3; %83%88%E3%82%99%20ver.1.4.pdf>; w/Machine Translation; Cited in Written Opposition dated Jan. 27, 2023.
Exhibit No. 7-5-Medi-EYE User's Guide ver. 1.5 <https://medi-lx.jp/images/upload/Medi-EYE%E3%83%A6%E3%83%BC%E3%82%B5%E3%82%99%E3%83%BC%E3%82%B9%E3%82%99%E3%82%AB%E3%82%99%E3%82%A4%E3%83%88%E3%82%99%20ver.1.5.pdf>; w/Machine Translation; Cited in Written Opposition dated Jan. 27, 2023.
Exhibit No. 7-6-Medi-EYE User's Guide ver. 1.6 <https://medi-lx.jp/images/upload/Medi-EYE%E3%83%A6%E3%83%BC%E3%82%B5%E3%82%99%E3%83%BC%E3%82%B9%E3%82%99%E3%82%AB%E3%82%99%E3%82%A4%E3%83%88%E3%82%99%20ver.1.6.pdf>; w/Machine Translation; Cited in Written Opposition dated Jan. 27, 2023.
Exhibit No. 7-7-Medi-EYE User's Guide ver. 1.7 <https://medi-lx.jp/images/upload/Medi-EYE%E3%83%A6%E3%83%BC%E3%82%B5%E3%82%99%E3%83%BC%E3%82%B9%E3%82%99%E3%82%AB%E3%82%99%E3%82%A4%E3%83%88%E3%82%99%20ver.1.7.pdf>; w/Machine Translation; Cited in Written Opposition dated Jan. 27, 2023.
Exhibit No. 7-8-Medi-EYE User's Guide ver. 1.8 <https://medi-lx.jp/images/upload/Medi-EYE%E3%83%A6%E3%83%BC%E3%82%B5%E3%82%99%E3%83%BC%E3%82%B9%E3%82%99%E3%82%AB%E3%82%99%E3%82%A4%E3%83%88%E3%82%99%20ver.1.8.pdf>; w/Machine Translation; Cited in Written Opposition dated Jan. 27, 2023.
Exhibit No. 8-1-Output Document of https://web.archive.org/web/20210701000000 */medi-lx.jp showing archive record of <https://medi-lx.jp/>; Cited in Written Opposition dated Jan. 27, 2023.
Exhibit No. 8-2-Output Document of https://web.archive.org/web/20210125101513/ https://medi-lx.jp/ which is archive record of <https://medi-lx.jp/> archived on Jan. 25, 2021; w/Partial Machine Translation; Cited in Written Opposition dated Jan. 27, 2023.
Exhibit No. 8-3-Output Document of https://web.archive.org/web/20210125094003/ https://medi-lx.jp/servise_medical-eye/ which is archive record of <https://medi-lx.jp/servise_medical-eye/> archived on Jan. 25, 2021; w/Partial Machine Translation; Cited in Written Opposition dated Jan. 27, 2023.
Exhibit No. 8-4-Output Document of Source Cord of https://web.archive.org/web/20210125094003/ https://medi-lx.jp/servise_medical-eye/ which is archive record of <https://medi-lx.jp/servise_medical-eye/>; Cited in Written Opposition dated Jan. 27, 2023.
Exhibit No. 8-5-Output Document of https://web.archive.org/web/20210227183326/ https://medi-lx.jp/ which is archive record of <https://medi-lx.jp/> archived on Feb. 27, 2021; w/Partial Machine Translation; Cited in Written Opposition dated Jan. 27, 2023.
Exhibit No. 8-6-Output Document of https://web.archive.org/web/20210227175602/ https://medi-lx.jp/servise_medical-eye/; which is archive record of; https://medi-lx.jp/servise_medical-eye/ archived on Feb. 27, 2021; w/Partial Machine Translation; Cited in Written Opposition dated Jan. 27, 2023.
Exhibit No. 8-7-Output Document of Source Cord of https://web.archive.org/web/20210227175602/ https://medi-lx.jp/servise_medical-eye/ which is archive record of <https://medi-lx.jp/servise_medical-eye/>; Cited in Written Opposition dated Jan. 27, 2023.
Exhibit No. 8-8-Output Document of https://web.archive.org/web/20210227183711/ https://medi-lx.jp/infomation-medi-eye/4 which is archive record of <https://medi-lx.jp/infomation-medi-eye/> archived on Feb. 27, 2021; w/Partial Machine Translation; Cited in Written Opposition dated Jan. 27, 2023.
Exhibit No. 9-News on website of Kyoritsu Women's University and Kyoritsu Women's Junior College showing use of Medi-EYE: <https://www.kyoritsu-wu.ac.jp/academics/undergraduate/kango/news/detail.html?id=2800>; w/Partial Machine Translation; Cited in Written Opposition dated Jan. 27, 2023.
A Written Opposition to the Grant of a Patent dated Jan. 27, 2023, issued in corresponding Japanese Patent No. 7087228 (Application No. 2021-163078), with English translation. (140 pages).

* cited by examiner

ADMINISTRATION SCREEN    LOGOUT

IMPORT EXCEL FILE DATA
*PLEASE UPLOAD EXCEL FILE AS FILE FORMAT

[SELECT FILE]    NOT SELECTED

[START TO IMPORT EXCEL FILE]

Figure 7(b)

ADMINISTRATION SCREEN  LOGOUT

214

IMPORT EXCEL FILE DATA
SUCCEED IN IMPORTING CSV DATA.  PLEASE CHECK ADMINISTRATION SCREEN.

| SELECT FILE | NOT SELECTED |

| START TO IMPORT CSV |

FILE UPLOAD LIST
16 FILES UPLOADED

UPLOAD DATE AND TIME 2020/09/05 06:43:39
FILE NAME af92594ed0afdc0ccce6c22d0a670063edc45490b.xlsx    DOWNLOAD FILE    DELETE FILE UPLOAD DATE AND TIME 2020/09/03 16:18:15
FILE NAME 64a03be6a3edbfa9f02cf7bb3beae2e9d03d67a4.xlsx    DOWNLOAD FILE    DELETE FILE UPLOAD DATE AND TIME 2020/09/03 16:18:4
FILE NAME cd665d8db34d83d0d61eee2ffc4b591e0f756ccb.xlsx    DOWNLOAD FILE    DELETE FILE

Figure 8(a)

ADMINISTRATION SCREEN  LOGOUT

215

| COPY | PATIENT NUMBER | PATIENT NAME | MAIN DEPARTMENT | AGE | FLOOR NUMBER OF ADMISSION HOSPITAL BED | ADMISSION HOSPITAL BED | DISPLAY NORMAL/ABNORMAL OF EXAMINATION | DISPLAY/NON-DISPLAY OF NURSING PLAN | SETTING SCREEN |
|---|---|---|---|---|---|---|---|---|---|
| ☑ | 0000023497 | TOKUDA KAZUO | DEPARTMENT OF UROLOGY | 75 YEARS OLD | 1ST FLOOR | 101 | ☑ | ☑ | MOVE |
| ☐ | 0000021945 | UCHIDA KEIJI | DEPARTMENT OF NEUROSURGERY | 79 YEARS OLD | 1ST FLOOR | 102 | ☑ | ☑ | MOVE |
| ☐ | 0000022560 | HORITA MAKIKO | DEPARTMENT OF OBSTETRICS | 32 YEARS OLD | 1ST FLOOR | 103 | ☑ | ☑ | MOVE |
| ☐ | 0000021950 | HORITA SOUTA | DEPARTMENT OF OBSTETRICS | 0 MONTHS OLD | 1ST FLOOR | 104 | ☑ | ☑ | MOVE |
| ☐ | 0000024038 | KAWAI YOSHIYUKI | DEPARTMENT OF PEDIATRICS | 9 YEARS OLD | 1ST FLOOR | 105 | ☑ | ☑ | MOVE |
| ☐ | 0000021944 | MORIYA TOSHIO | DEPARTMENT OF PSYCHIATRY | 39 YEARS OLD | 1ST FLOOR | 106 | ☑ | ☑ | MOVE |
| ☐ | 0000022060 | OHNO KYOKO | DEPARTMENT OF PSYCHIATRY | 54 YEARS OLD | 1ST FLOOR | 107 | ☑ | ☑ | MOVE |
| ☐ | 0000024240 | KAWASAKI YOSHIYUKI | DEPARTMENT OF PEDIATRICS | 6 YEARS OLD | 1ST FLOOR | 108 | ☑ | ☑ | MOVE |
| ☐ | 0000024447 | ICHO KYOKO | DEPARTMENT OF PEDIATRICS | 4 YEARS OLD | 1ST FLOOR | 109 | ☑ | ☑ | MOVE |
| ☐ | 0000025659 | TAMURA KAZUO | DEPARTMENT OF UROLOGY | 75 YEARS OLD | 1ST FLOOR | 110 | ☐ | ☐ | MOVE |

COPY CHECKED DATA

Figure 8(b)

ADMINISTRATION SCREEN   LOGOUT

216

| USE ☐ | PATIENT NUMBER | PATIENT NAME | MAIN DEPARTMENT | AGE | FLOOR NUMBER OF ADMISSION HOSPITAL BED | ADMISSION HOSPITAL BED | DISPLAY EXAMINATION REFERENCE VALUE ☐ | DISPLAY NURSING PLAN ☐ | SETTING SCREEN |  |
|---|---|---|---|---|---|---|---|---|---|---|
| ☑ | 0000028696 | TOKUDA KAZUO | DEPARTMENT OF UROLOGY | 75 YEARS OLD | 1ST FLOOR ˅ | 100 | ☑ | ☑ | SET | DELETE |
| ☐ | 0000031490 | TOKUDA KAZUO | DEPARTMENT OF UROLOGY | 75 YEARS OLD | 1ST FLOOR ˅ | 100 | ☑ | ☑ | SET | DELETE |
| ☑ | 0000028692 | UCHIDA KEIJI | DEPARTMENT OF NEUROSURGERY | 79 YEARS OLD | 1ST FLOOR ˅ | 101 | ☑ | ☑ | SET | DELETE |
| ☑ | 0000028688 | NOZAKI ICHIRO | DEPARTMENT OF INTERNAL MEDICINE | 78 YEARS OLD | 1ST FLOOR ˅ | 102 | ☑ | ☑ | SET | DELETE |
| ☑ | 0000028693 | NAKAI HIROSHI | DEPARTMENT OF CARDIOVASCULAR MEDICINE | 82 YEARS OLD | 1ST FLOOR ˅ | 103 | ☑ | ☑ | SET | DELETE |
| ☑ | 0000028689 | KURISU ASAMI | DEPARTMENT OF PEDIATRICS | 1 YEAR AND 8 MONTHS OLD | 1ST FLOOR ˅ | 104 | ☑ | ☑ | SET | DELETE |
| ☑ | 0000028695 | KAWASAKI YOSHIYUKI | DEPARTMENT OF PEDIATRICS | 6 YEARS OLD | 1ST FLOOR ˅ | 105 | ☑ | ☑ | SET | DELETE |
| ☑ | 0000028691 | HORITA MAKIKO | DEPARTMENT OF OBSTETRICS | 32 YEARS OLD | 1ST FLOOR ˅ | 106 | ☑ | ☑ | SET | DELETE |

Figure 10(b)

ADMINISTRATION SCREEN  LOGOUT

201

NEW REGISTRATION

| LEARNER ID | LEARNER PASS | LEARNING SETTING SCREEN | PATIENT SETTING SCREEN | |
|---|---|---|---|---|
| 111111 | Mekata1212 | EDIT | MOVE | DELETE |

GO BACK

Figure 12

ADMINISTRATION SCREEN  LOGOUT

202

| USE | PATIENT NUMBER | LAST NAME OF PATIENT | FIRST NAME OF PATIENT | FLOOR NUMBER OF ADMISSION HOSPITAL BED | ADMISSION HOSPITAL BED |
|---|---|---|---|---|---|
| ☑ | 0000000003 | TAMARU | JIRO | 1ST FLOOR | 101 |
| ☑ | 0000000004 | SHINYA | TAIZO | 1ST FLOOR | 102 |
| ☑ | 0000000005 | ASADA | TARO | 2ND FLOOR | 201 |
| ☑ | 0000000006 | KARIYA | CHIE | 2ND FLOOR | 202 |
| ☑ | 0000000012 | KAWAI | YOSHIYUKI | 4TH FLOOR | 401 |
| ☑ | 0000000013 | MORIYA | TOSHIO | 5TH FLOOR | 501 |
| ☐ | 0000000014 | NAGASHIMA | EMI | 5TH FLOOR | 502 |
| ☐ | 0000000023 | FURO | AOTO | 3RD FLOOR | 302 |
| ☐ | 0000000024 | FURO | SOUTA | 3RD FLOOR | 303 |
| ☐ | 0000000028 | UMEKI | HANAKO | 3RD FLOOR | 306 |
| ☐ | 0000000030 | FURO | MAKIKO | 3RD FLOOR | 301 |
| ☐ | 0000000032 | SHINYA | TAIZO | FLOOR | |
| ☐ | 0000000033 | SHINYA | TAIZO | FLOOR | |
| ☐ | 0000000034 | KAWAI | YOSHIYUKI | FLOOR | |
| ☐ | 0000000038 | UMEKI | KANAKO | 3RD FLOOR | 311 |

GO BACK  UPDATE

Figure 14

ADMINISTRATION SCREEN    LOGOUT    203

| USE | PATIENT NUMBER | LAST NAME OF PATIENT | FIRST NAME OF PATIENT | FLOOR NUMBER OF ADMISSION HOSPITAL BED | ADMISSION HOSPITAL BED | DISPLAY NORMAL/ABNORMAL OF EXAMINATION | DISPLAY/NON-DISPLAY OF NURSING PLAN | SETTING SCREEN |
|---|---|---|---|---|---|---|---|---|
| DELETE ☑ | 0000000003 | TAMARU | JIRO | PLEASE SELECT ✓ 1ST FLOOR / 2ND FLOOR / 3RD FLOOR / 4TH FLOOR / 5TH FLOOR / 6TH FLOOR / 7TH FLOOR / 8TH FLOOR / 9TH FLOOR / 10TH FLOOR | | ☐ | ☐ | MOVE |
| DELETE ☑ | 0000000004 | SHINYA | TAIZO | | | ☐ | ☐ | MOVE |
| DELETE ☑ | 0000000005 | ASADA | TARO | | | ☐ | ☐ | MOVE |
| DELETE ☑ | 0000000006 | KARIYA | CHIE | | | ☐ | ☐ | MOVE |
| DELETE ☑ | 0000000012 | KAWAI | YOSHIYUKI | | | ☐ | ☐ | MOVE |
| DELETE ☑ | 0000000013 | MORIYA | TOSHIO | | | ☐ | ☐ | MOVE |
| DELETE ☑ | 0000000014 | NAGASHIMA | EMI | 5TH FLOOR ∨ | 502 | ☐ | ☐ | MOVE |
| DELETE ☑ | 0000000023 | FURO | AOTO | 3RD FLOOR ∨ | 302 | ☐ | ☐ | MOVE |
| DELETE ☑ | 0000000024 | FURO | SOUTA | 3RD FLOOR ∨ | 303 | ☐ | ☐ | MOVE |

GO BACK  UPDATE

Figure 15

ADMINISTRATION SCREEN  LOGOUT

ADMINISTRATOR SCREEN

BED MAP

SELECT HOSPITAL WARD ▶

HOSPITAL WARD: 1ST FLOOR

| 101 KANDA TAKESHI<br>DEPARTMENT OF RESPIRATORY SURGERY  82 YEARS OLD | 102 IWAMOTO TOSHIO<br>DEPARTMENT OF INTERNAL MEDICINE  70 YEARS OLD | 103 YAMADA MIKA<br>DEPARTMENT OF PSYCHIATRY  40 YEARS OLD | 104 NOZAKI ICHIRO<br>DEPARTMENT OF INTERNAL MEDICINE  78 YEARS OLD | 105 YAMADA MUTSUKI<br>DEPARTMENT OF PEDIATRIC SURGERY  1 YEAR AND 9 MONTHS OLD |
| --- | --- | --- | --- | --- |
| 106 AKIHARA TADASHI<br>DEPARTMENT OF GENERAL MEDICINE  40 YEARS OLD | 107 MATSUDA NAOTO<br>DEPARTMENT OF CARDIOVASCULAR MEDICINE  52 YEARS OLD | 108 TANAKA MICHIKO<br>DEPARTMENT OF RESPIRATORY SURGERY  69 YEARS OLD | 109 IBUKI YOKO<br>DEPARTMENT OF OBSTETRICS  29 YEARS OLD | 110 IBUKI RIKO<br>DEPARTMENT OF OBSTETRICS  0 MONTHS OLD |
| 111 NAGASHIMA KAZUMI | 112 NAGASHIMA EITA | 113 KURISU ASAMI | | |

| PATIENT NUMBER | PATIENT | HOSPITAL ADMISSION DATE AND TIME | HOSPITAL DISCHARGE DATE AND TIME | HOSPITAL ADMISSION START DATE AND TIME | DISPLAY END DATE AND TIME |
|---|---|---|---|---|---|
| 0000000038 | UMEKI KANAKO | 2018-01-02 | 2018-01-06 | 2020-09-02 | 2020-09-05 09:00:0 |

GO BACK | UPDATE

ADMINISTRATION SCREEN  LOGOUT

205

SEPTEMBER 2020

| SUN | MON | TUE | WED | THU | FRI | SAT |
|---|---|---|---|---|---|---|
| 30 | 31 | 1 | 2 | 3 | 4 | 5 |
| 6 | 7 | 8 | 9 | 10 | 11 | 12 |
| 13 | 14 | 15 | 16 | 17 | 18 | 19 |
| 20 | 21 | 22 | 23 | 24 | 25 | 26 |
| 27 | 28 | 29 | 30 | 1 | 2 | 3 |

ADMINISTRATION SCREEN   LOGOUT

206

EXAMINATION ORDER INFORMATION

* IS MANDATORY

ORDER DATE*
2020-09-02

ORDER TIME*
08:00:00

REQUESTED DIAGNOSIS AND TREATMENT DEPARTMENT*
DEPARTMENT OF OBSTETRICS

EXAMINATION TYPE*
ULTRASONIC EXAMINATION*

IMAGE 1
SELECT FILE   NOT SELECTED

ADMINISTRATOR SCREEN

ADMINISTRATION SCREEN    LOGOUT

UMEKI KANAKO    AGE:22    BLOOD TYPE:O    HEIGHT:162    WEIGHT:55    ALLERGY:POLLINOSIS    INFECTION:NONE

- BLOOD EXAMINATION
- BLOOD GAS
- BACTERIAL PATHOGENESIS
- FUNCTION EXAMINATION
- IMAGE EXAMINATION

PATHOLOGICAL
EXAMINATION
:2020-08-03
 08:15

| RESULT OF URINE QUALITATIVE | |
|---|---|
| SUGAR | - |
| pH | 5.2 |
| KETONE BODY | - |
| PROTEIN | - |
| BILIRUBIN | - |
| OCCULT BLOOD TEST | - |
| UROBILINOGEN | +/- |
| WHITE BLOOD CELL | - |
| NITRITE | - |
| COLOR | PALE YELLOW |
| CLARITY | 1+ |
| SPECIFIC GRAVITY | 1.011 |

Figure 22

| BED MAP | ADMINISTRATOR SCREEN | | | | ADMINISTRATION SCREEN | LOGOUT |

HOSPITAL ADMISSION: HOSPITAL ROOM 311  UMEKI KANAKO  AGE: 22  BLOOD TYPE: O  HEIGHT: 162.0  WEIGHT AT HOSPITAL  ALLERGY: POLLINOSIS  INFECTION: NONE
DIAGNOSIS AND TREATMENT DEPARTMENT: DEPARTMENT OF OBSTETRICS                                   ADMISSION: 55.0
                                                                            UPDATE  DATA EDITING MODE

| | PATIENT NUMBER1 | PATIENT NUMBER2 | PATIENT NUMBER3 | | DISORDER INFORMATION |
|---|---|---|---|---|---|
| PATIENT BASIC INFORMATION | PATIENT NUMBER | 0000000038 | | | DISORDER |
| MEDICAL RECORD | FULL NAME OF PATIENT | UMEKI | KANAKO | | |
| TEMPERATURE CHECK TABLE | KANA NAME OF PATIENT | | | | DISEASE INFORMATION |
| MEDICATION | DATE OF BIRTH | | | | DISEASE |
| INJECTION | ADDRESS | OSAKA PREFECTURE | | | ANAMNESIS |
| GENERAL INSTRUCTION | TYPE OF INSURANCE | NATIONAL HEALTH INSURANCE | | | ONSET DATE  STATE  DISEASE |
| EXAMINATION RESULT | BLOOD TYPE (ABO SYSTEM) | O | | | PATIENT STATE INFORMATION |
| ORDER HISTORY | BLOOD TYPE (Rh SYSTEM) | Rh+ | | | DATE AND TIME | START: 2018-01-02  END: 2018-01-02 |
| NURSING SUPPORT | RELIGION/FAITH | BUDDHISM | | | FIRST-AID CATEGORY | ESCORT |
| DOCUMENT/REPORT | GENDER | Bigender HAVING BOTH MALE AND FEMALE GENDERS | | | BED REST LEVEL | III°b AMBULANT IN HOSPITAL ROOM AND RESTROOM HOUSE CALL WHEELCHAIR ACCESSIBLE |
| | MENOPAUSE | | | | OBSERVATION LEVEL | B CONTINUOUS OBSERVATION IS REQUIRED |
| | FREE COMMENT | | | | | |

EDUCATIONAL ELECTRONIC HEALTH RECORD SYSTEM AND EDUCATIONAL ELECTRONIC HEALTH RECORD PROGRAM

TECHNICAL FIELD

The present invention relates to an educational electronic health record system and an educational electronic health record program that enable education and training using an electronic health record for, for example, a medical service worker or the like.

BACKGROUND ART

A medical educational institute is required to develop advanced medical practice capability in an environment surrounding a medical setting as well as in the course of advancement and complication of a medical treatment, various needs of a patient, and advancement of information. For example, a nursing student or the like is required to have capability for practicing suitable nursing such as collecting information using an electronic health record or the like, accurately grasping and analyzing the state of a patient, based on the collected information, and preparing a nursing plan. In the education and the training of such practice capability, practical case learning is effective, and in nursing education, extramural activity such as clinical practice is also incorporated in the curriculum, in addition to learning activity in school.

However, there are few educational materials with good quality, and an educational electronic health record of the related art is only for the nursing student or the like to experience the manipulation of an electronic health record. In addition, the utilization of a medical simulation or a nursing learning system is also considered, but the medical simulation or the nursing learning system does not include a large amount of information such as a clinical chart used in the actual medical setting, and is only capable of providing the learning from the collection of information at a specific stage to the performance of a nursing action. Accordingly, it is difficult to sufficiently perform the education and the training of the practice capability, such as preparing the nursing plan (refer to Patent Literature 1).

CITATION LIST

Patent Literature

Patent Literature 1: JP-A-2015-219247

SUMMARY OF THE INVENTION

Technical Problem

The present invention has been made in consideration of the problems described above, and an object thereof is to provide an educational electronic health record system and educational electronic health record program that enable the use of patient health record information having an information amount greater than or equal to that of an electronic health record used in the actual medical setting by responding to various needs of a learner or advanced and complicated medical information, and thus, enable effective education and training for the learner such as a medical service worker.

Solution to Problem

In order to attain the object described above, an educational electronic health record system of the present invention is an educational electronic health record system including at least a learner terminal, and an educational electronic health record server to the learner terminal through a network, in which the educational electronic health record server includes a data file acquisition unit acquiring a data file that is described in a data format of an arbitrary software and includes simulated patient information, a storage unit storing the simulated patient information of the data file acquired by the data file acquisition unit, and a patient health record information generation unit calling the simulated patient information from the storage unit and generating patient health record information displayed on the learner terminal, based on the simulated patient information.

According to the configuration described above, the educational electronic health record server (hereinafter, may be referred to as an "electronic health record server") is capable of causing the data file acquisition unit to import the data file described in the data format of arbitrary software from the outside, and the storage unit to store the simulated patient information included in the data file. In addition, the electronic health record server is capable of causing the patient health record information generation unit to generate the patient health record information displayed on the learner terminal, based on the simulated patient information stored in the storage unit. Accordingly, in the configuration described above, it is possible to use the patient health record information having an information amount greater than or equal to that of an electronic health record used in the actual medical setting by responding to various needs of a learner or advanced and complicated medical information, and thus, to perform effective education and training for the learner.

In the configuration described above, the educational electronic health record server may further include a display condition setting unit setting a display condition of the patient health record information displayed on the learner terminal, and the patient health record information generation unit may call the simulated patient information from the storage unit adequate for the display condition set by the display condition setting unit and generate the patient health record information, based on the called simulated patient information.

According to the configuration described above, for example, it is possible to change the patient health record information to be displayed, in accordance with the contents desired to be learned, a learning achievement degree of the learner, the needs of the learner, and the like. As a result thereof, it is possible to perform more effective education and training for the learner.

Further, in the configuration described above, the simulated patient information stored in the storage unit may be associated with arbitrary information included in the simulated patient information and include virtually set date and time information, the display condition setting unit may set a date and time different from a date and time included in the date and time information, and the patient health record information generation unit may generate the patient health record information displayed on the learner terminal, based on the date and time set by the display condition setting unit.

According to the configuration described above, the display condition setting unit sets a new date and time different from the date and time of the date and time information included in the simulated patient information, and thus, it is possible to cause the patient health record information generation unit to generate the patient health record information, based on the newly set date and time. Accordingly, it is possible to coordinate a display date and time of the patient health record information displayed on the learner terminal with a practice/exercise start date and time of the learner. In addition, it is possible to perform more effective education and training for the learner by repeating a time course such as clinical practice.

In addition, in the configuration described above, the storage unit may store at least information that is associated with the simulated patient information and is relevant to a virtually set patient placement location, and the patient health record information generation unit may call the information relevant to the patient placement location and the simulated patient information stored in the storage unit, based on the display condition set by the display condition setting unit, and generate the patient health record information including the information relevant to the patient placement location.

According to the configuration described above, it is possible to generate the patient health record information including the information relevant to the patient placement location (for example, patient placement information such as a hospital ward, a hospital room, and a hospital bed), based on the condition set by the display condition setting unit.

In addition, in the configuration described above, the educational electronic health record server may further include a patient health record information editing unit editing the patient health record information generated by the patient health record information generation unit, and the patient health record information editing unit may update the simulated patient information stored in the storage unit, based on new patient health record information edited by the patient health record information editing unit.

According to the configuration described above, it is possible to freely edit the patient health record information generated based on the simulated patient information that is imported by acquiring the data file, and thus, it is possible to improve the degree of freedom of the education and training for a medical service worker or the like, such as enabling exercise and practice according to various case histories or the like.

In addition, in order to attain the object described above, an educational electronic health record program of the present invention is a computer-readable educational electronic health record program for causing an educational electronic health record server connected to a learner terminal through a network to execute processing for acquiring a data file that is described in a data format of arbitrary software and includes simulated patient information, processing for storing the acquired simulated patient information in a storage unit of the educational electronic health record server, and processing for calling the simulated patient information from the storage unit and generating patient health record information displayed on the learner terminal, based on the simulated patient information.

According to the configuration described above, the educational electronic health record program (hereinafter, may be referred to as an "electronic health record program") causes the educational electronic health record server to execute the processing for importing the data file described in the data format of arbitrary software from the outside, and of storing the simulated patient information included in the data file in the storage unit. In addition, the electronic health record program causes the educational electronic health record server to execute the processing for generating the patient health record information displayed on the learner terminal, based on the simulated patient information stored in the storage unit. Accordingly, in the electronic health record program of the configuration described above, by using the simulated patient information having an information amount greater than or equal to that of the electronic health record used in the actual medical setting, it is possible to sufficiently perform education and training for the learner, such as preparing a nursing plan and an action plan.

In the configuration described above, the program may cause the educational electronic health record server to further execute processing for setting a display condition of the patient health record information displayed on the learner terminal, and processing for calling the simulated patient information adequate for the set display condition from the storage unit and generating the patient health record information, based on the called simulated patient information.

According to the configuration described above, for example, it is possible to change the patient health record information to be displayed, in accordance with the contents desired to be learned, a learning achievement degree of the learner, the needs of the learner, and the like. As a result thereof, it is possible to perform more effective education and training for the learner.

In the configuration described above, the simulated patient information stored in the storage unit may be associated with information included in the simulated patient information and may include virtually set date and time information, and the program may cause the educational electronic health record server to further execute processing for setting a date and time different from a date and time included in the date and time information, and processing for generating the patient health record information displayed on the learner terminal, based on the set date and time.

According to the configuration described above, by setting a new date and time different from the date and time of the date and time information included in the simulated patient information, it is possible to generate the patient health record information, based on the newly set date and time. Accordingly, it is possible to coordinate a display date and time of the patient health record information displayed on the learner terminal with a practice/exercise start date and time of the learner. In addition, it is possible to perform more effective education and training for the learner by repeating a time course such as clinical practice.

In addition, in the configuration described above, the storage unit may store at least information that is associated with the simulated patient information and is relevant to a virtually set patient placement location, and the program may cause the educational electronic health record server to further execute processing for calling the information relevant to the patient placement location and the simulated patient information from the storage unit, based on the set display condition, and generating the patient health record information including the information relevant to the patient placement location.

According to the configuration described above, it is possible to generate the patient health record information including the information relevant to the patient placement location (for example, the patient placement information such as the hospital ward, the hospital room, and the hospital bed), based on the display condition.

In addition, in the configuration described above, the program may allow the educational electronic health record server to further execute processing for editing the generated patient health record information and updating the simulated patient information stored in the storage unit, based on edited new patient health record information.

According to the configuration described above, it is possible to freely edit the patient health record information generated based on the simulated patient information that is imported by acquiring the data file, and thus, it is possible to improve the degree of freedom of the education and training for a medical service worker or the like, such as enabling exercise and practice according to various case histories or the like.

Advantageous Effects of Invention

According to the present invention, by responding to various needs of the learner or the advanced and complicated medical information, it is possible to use the simulated patient information having an information amount greater than or equal to that of the electronic health record used in the actual medical setting. Accordingly, for example, it is possible to provide the educational electronic health record system and the educational electronic health record program that enable effective education and training for the learner, and the acquisition of required knowledge and skill, even in a case where it is difficult to substitute a practice facility or the like, in the clinical practice or the like.

BRIEF DESCRIPTION OF THE FIGURES

FIG. 7(a) is an explanatory diagram illustrating an upload reception screen page of a data file, and FIG. 7(b) is an explanatory diagram illustrating an upload completion screen page after upload.

FIG. 8(a) is an explanatory diagram illustrating a simulated patient information copy screen page for performing simulated patient information copy processing, FIG. 8(b) is an explanatory diagram illustrating a simulated patient information copy completion screen page.

FIG. 10(b) is an explanatory diagram illustrating a registered learner administration page indicating a registered learner.

FIG. 12 is an explanatory diagram illustrating a simulated patient setting page for setting a simulated patient displayed to the registered learner.

FIG. 14 is an explanatory diagram illustrating a simulated patient information setting page for setting selected simulated patient information.

FIG. 15 is an explanatory diagram illustrating a bed map display page displaying information relevant to a patient placement location in the hospital ward.

FIG. 17(a) and FIG. 17(b) are explanatory diagrams illustrating a date and time display setting page for changing date and time display of the patient health record information.

FIG. 19(a) is an explanatory diagram illustrating an examination order history information registration page for registering information relevant to an examination order history, and FIG. 19(b) is an explanatory diagram illustrating a web page displaying image data in which various examination results are described.

FIG. 22 is an explanatory diagram illustrating an electronic health record editing page displayed on the administrator terminal.

DETAILED DESCRIPTION OF THE INVENTION (Educational Electronic Health Record System)

An educational electronic health record system according to an embodiment of the present invention (hereinafter, may be referred to as an "electronic health record system") and an educational electronic health record program (hereinafter, may be referred to as an "electronic health record program") will be described below with reference to the drawings.

[Overall Configuration of Educational Electronic Health Record System]

Figure 1:
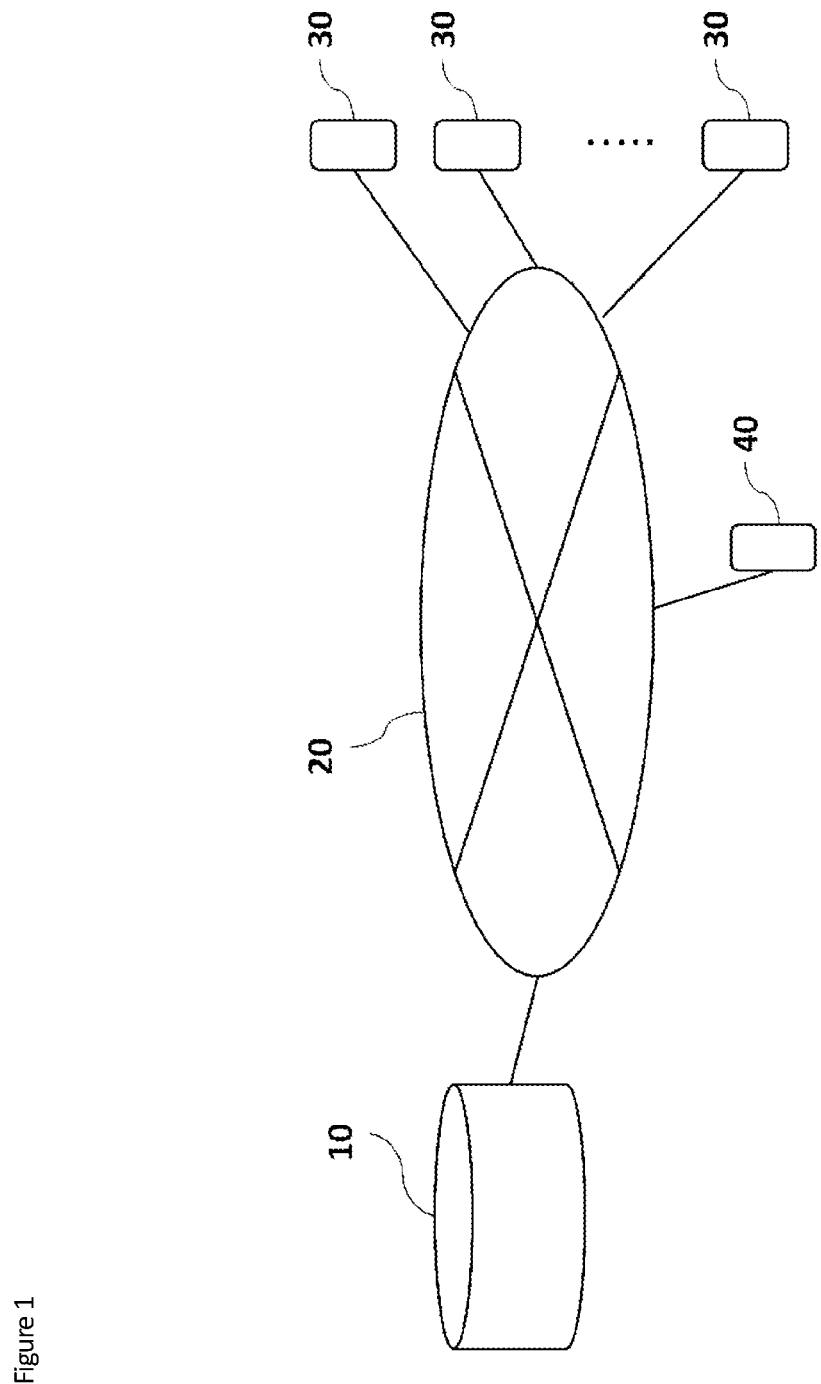
FIG. 1 is a conceptual diagram illustrating an example of a configuration of an educational electronic health record system according to an embodiment of the present invention.

As illustrated in FIG. 1, in the electronic health record system of this embodiment, an educational electronic health record server (hereinafter, referred to as an "electronic health record server") 10, a learner terminal 30 used by a learner, and an administrator terminal 40 used by an administrator are connected to each other through a network 20 such that communication can be performed. FIG. 1 is a conceptual diagram illustrating an example of the configuration of the educational electronic health record system according to this embodiment.

The electronic health record server 10, for example, is realized by executing an electronic health record program in a workstation, a personal computer, or other computer devices. The electronic health record server 10 stores simulated patient information, and displays patient health record information generated based on the simulated patient information on the learner terminal 30, and thus, enables education and training using an educational electronic health record for the learner (the details of the simulated patient information and the patient health record information will be described below).

Figure 2:
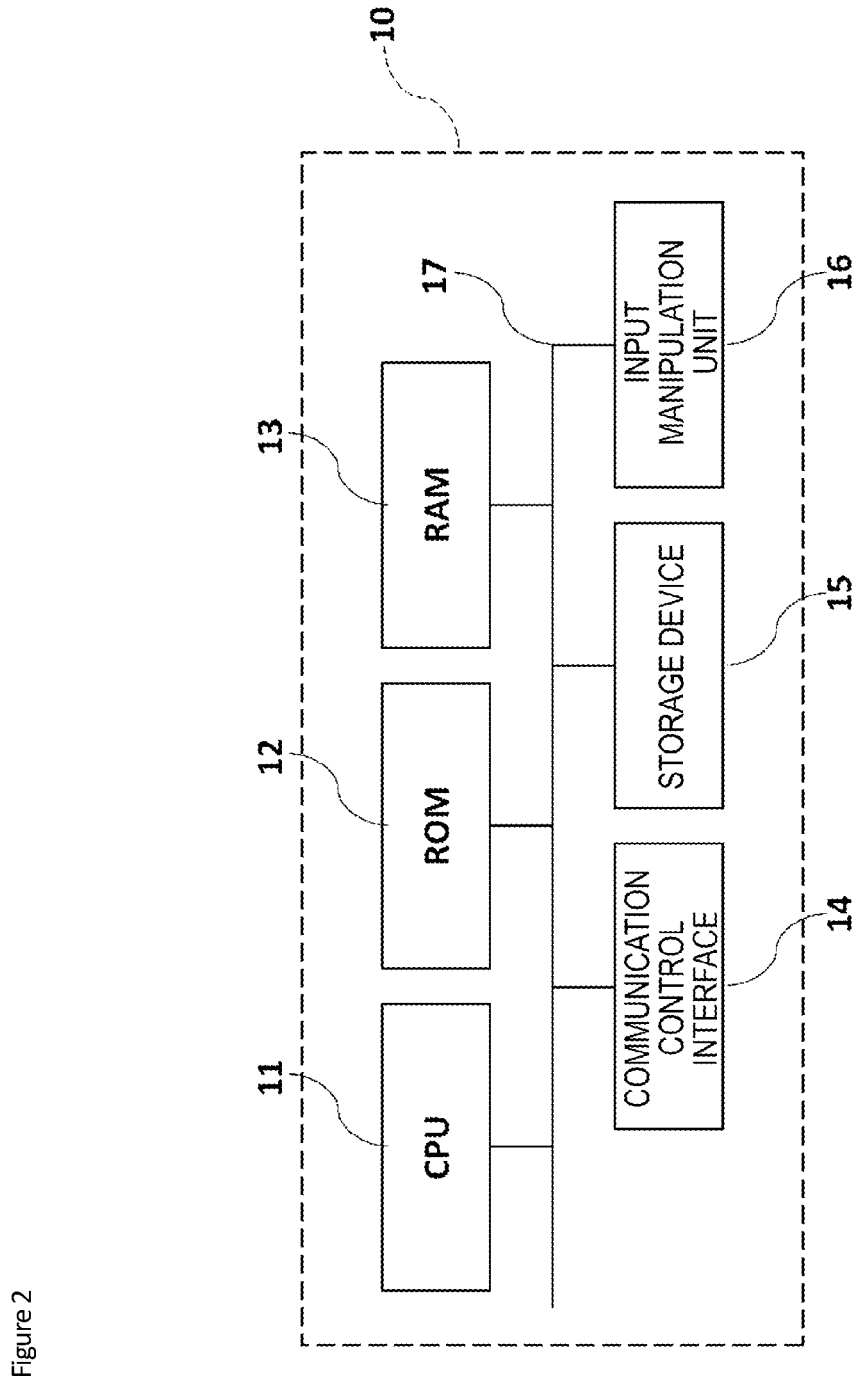
FIG. 2 is a block diagram illustrating a hardware configuration of an electronic health record server according to the embodiment of the present invention.

Specifically, a hardware configuration of the electronic health record server 10, for example, is as follows. That is, as illustrated in FIG. 2, the electronic health record server 10 includes at least a central processing unit (CPU) 11, a read only memory (ROM) 12, a random access memory (RAM) 13, a communication control interface 14, a storage device 15, and an input manipulation unit 16. FIG. 2 is a block diagram illustrating the hardware configuration of the electronic health record server 10.

The CPU 11 performs various arithmetic processing and the like for controlling the entire electronic health record server 10. More specifically, the CPU 11 reads out the electronic health record program from the ROM 12, and executes electronic health record program by using the RAM 13 as the workspace, and thus, controls the operation of each constituent of the electronic health record server 10. The ROM 12 is a read-only memory, and for example, stores an initial program or the like that is executed by the CPU 11 when activating the electronic health record server 10. The RAM 13 is a writable volatile memory, and transitorily stores a running program, data, or the like. The communication control interface 14 controls data transmission to the outside and controls data reception from the outside. The electronic health record server 10 is connected to the network 20 through the communication control interface 14 such that communication can be performed. The storage device 15, for example, includes a magnetic disk device or the like, and stores various programs and various data pieces to be retained even when a power source of the electronic health record server 10 is turned off. Specifically, the input manipulation unit 16 is a keyboard, a mouse, or the like, and receives an input manipulation from the administrator or the like.

The network 20 is realized by using various networks such as the internet, a dedicated line, wide area network (WAN), a lamp line network, a wireless network, a public network, and a mobile telephone network. Further, in the network 20, internet communication with improved security properties may be established by using a virtual dedicated network technology such as a virtual private network (VPN).

The learner terminal 30 is realized by a mobile terminal device such as a mobile telephone, a smart phone, a personal handy-phone system (PHS), and a personal digital assistant (PDA), an information processing device such as a desktop or laptop personal computer, and the like. In the electronic health record system of this embodiment, there may be at least one learner terminal 30, or there may be a plurality of learner terminals. In order to realize the electronic health record system of this embodiment, it is preferable that an internet browser or the like is mounted on the learner terminal 30.

Figure 3:
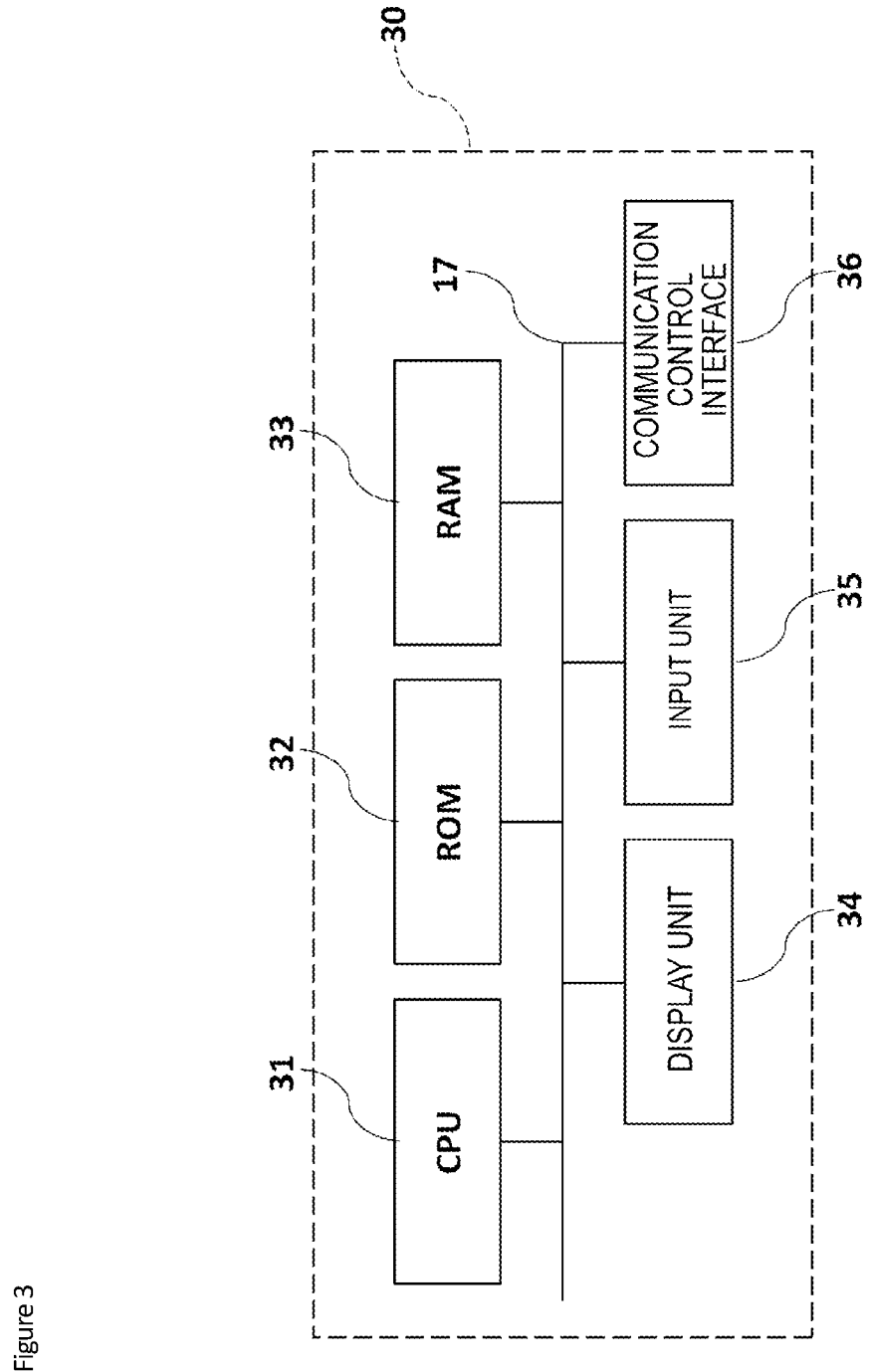
FIG. 3 is a block diagram illustrating a hardware configuration of a learner terminal according to the embodiment of the present invention.

Specifically, for example, a hardware configuration of the learner terminal 30 is as follows. That is, as illustrated in FIG. 3, the learner terminal 30 includes at least a CPU 31, a ROM 32, a RAM 33, a display unit 34, an input unit 35, and a communication control interface 36. FIG. 3 is a block diagram illustrating the hardware configuration of the learner terminal 30.

The CPU 31 performs various arithmetic processing and the like for controlling the entire learner terminal 30. More specifically, the CPU 31 reads out a computer program from the ROM 32, and executes the computer program by using the RAM 33 as the workspace, and thus, controls the operation of each constituent of the learner terminal 30. The ROM 32 is a writable non-volatile memory, and is capable of storing various program and various data pieces to be retained even when a power source of the learner terminal 30 is turned off. The RAM 33 is a writable volatile memory, and is capable of transitorily storing a running program, data, or the like. The display unit 34, for example, is realized by a liquid crystal display or an organic electroluminescence (EL) display, a monitor, a touch panel, or the like. The communication control interface 36 controls data transmission to the outside the learner terminal 30, and controls data reception from the outside. The learner terminal 30 is connected to the network 20 through the communication control interface 36 such that communication can be performed.

The administrator terminal 40 is realized by a mobile terminal device such as a mobile telephone, a smart phone, a PHS, and a PDA, an information processing device such as a desktop or laptop personal computer, and the like. In addition, as with the learner terminal 30, in the administrator terminal 40, a hardware configuration including at least a CPU, a ROM, a RAM, a display unit, an input unit, and a communication control interface can be adopted. Accordingly, the detailed description of a hardware configuration of the administrator terminal 40 will be omitted.

[Educational Electronic Health Record Server]

Figure 4:
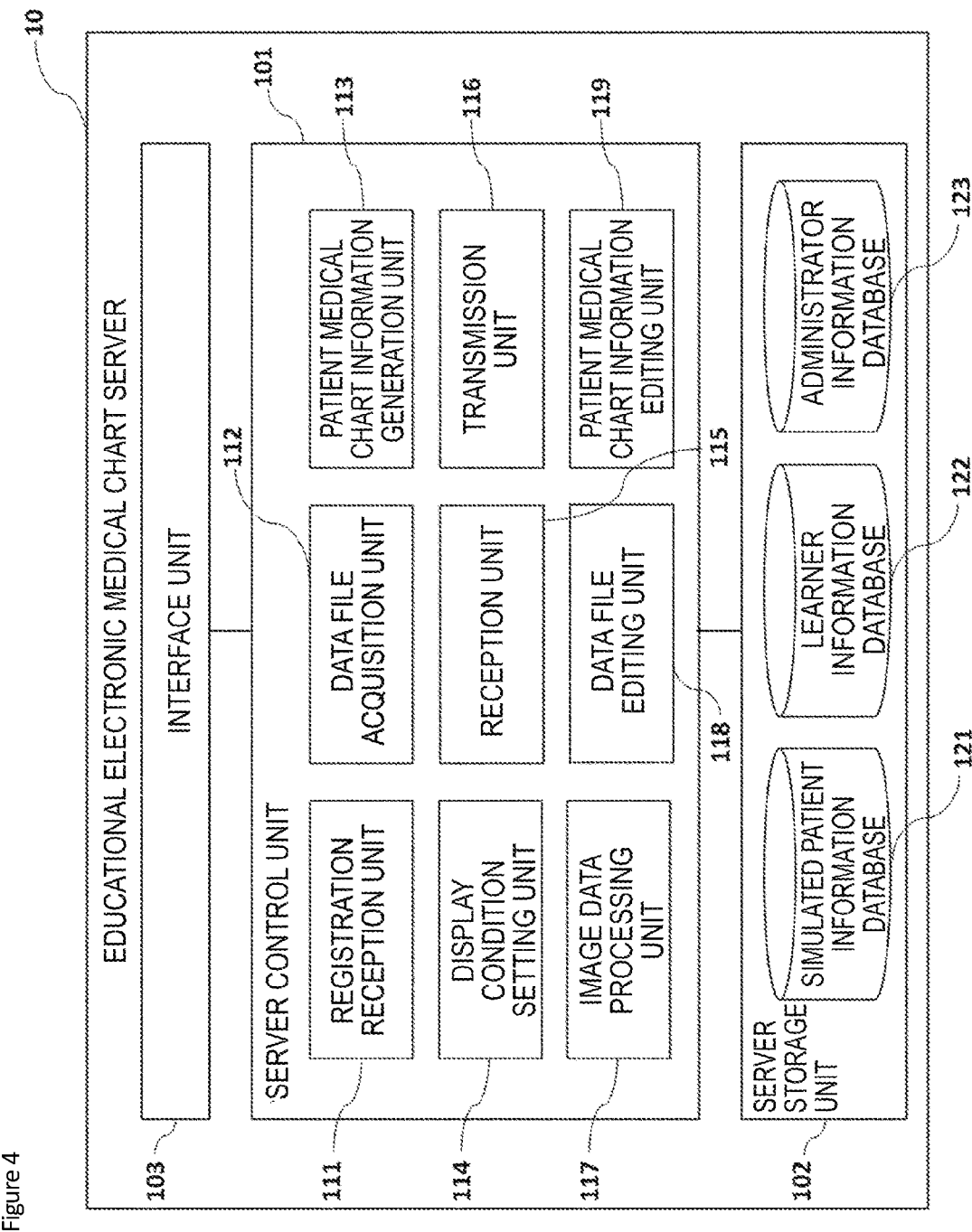
FIG. 4 is a block diagram illustrating an example of a function configuration of the electronic health record server according to the embodiment of the present invention.

Next, a function configuration of the electronic health record server 10 will be described based on FIG. 4. FIG. 4 is a block diagram illustrating an example of the function configuration of the electronic health record server 10. As illustrated in the same drawing, the electronic health record server 10 function-conceptually includes at least a server control unit 101, a server storage unit (a storage unit) 102, and an interface unit 103.

The server control unit 101 includes an internal memory for storing a control program such as OS, a program in which various processing procedures and the like are defined, and required data. The server control unit 101 performs information processing of executing various processing by such programs and the like. The server control unit 101 function-conceptually includes at least a registration reception unit 111, a data file acquisition unit 112, a patient health record information generation unit 113, a display condition setting unit 114, a reception unit 115, a transmission unit 116, an image data processing unit 117, a data file editing unit 118, and a patient health record information editing unit 119.

The registration reception unit 111 is means for receiving new registration of the administrator from the administrator terminal 40 or a change in registered entry. In addition, the registration reception unit 111 is means for receiving the registration and setting of the learner from the administrator terminal 40.

The data file acquisition unit 112, for example, is means for acquiring a data file including simulated patient information by a protocol such as file transfer protocol (FTP) through the network 20. In addition, the data file acquisition unit 112 stores the imported data file in a simulated patient information database 121 described below. By the data file acquisition unit 112 importing the data file including the simulated patient information to the electronic health record server 10, it is possible to flexibly respond to various needs of the learner. In addition, it is possible to respond to advanced and complicated medical information, the simulated patient information having an information amount greater than or equal to that of the electronic health record used in the actual medical setting can be implemented in the electronic health record server 10.

The simulated patient information, for example, indicates information including a simulated patient number; hospital admission information; patient basic information such as a simulated patient number, activity of daily living (ADL) before hospital admission, a living pattern, health administration information, domiciliary support information, inclination/decision-making support, disease information, anamnesis, patient state information, patient family information, patient job information, patient disorder information, patient allergic information, patient infectious disease information, a menstrual history, and TPAL; diagnosis and treatment department information; medical record (course) information; nursing performance information; nursing problem information; injection order information; medication order information; general instruction information; specimen examination result information; surgery order information; dialysis order information; rehabilitation order information; nursing support information, and the like. Note that, the simulated patient number is an identifier imparted corresponding to each simulated patient included in the simulated patient information, and for example, includes a number, a character, a symbol, or a combination thereof. In addition, in a case where the simulated patient number is not included in the simulated patient information imported by the data file acquisition unit 112, the simulated patient number is imparted corresponding to each simulated patient included in the simulated patient information when the data file acquisition unit 112 imports the data file.

In addition, it is preferable that the simulated patient information includes virtually set date and time information. The date and time information indicates information relevant to a hospital admission date and time, a hospital discharge date and time, or the like of the simulated patient in the past, the present, and the future. In addition, it is preferable that the date and time information is associated with information included in the simulated patient information. The information included in the simulated patient information indicates the hospital admission information or the like described above.

The data file is described in a data format of arbitrary software. The software is not particularly limited, and examples thereof include spreadsheet software and the like. Further, as the spreadsheet software, for example, Excel (Registered Trademark) or the like can be used. The data format is not particularly limited, and examples thereof include a text file such as a comma-separated value (CSV) format.

By creating the data file with the spreadsheet software that is routinely used by the administrator, it is possible to improve the standardization of the data format, the readability, and the maintainability. In addition, it is possible to use a calculated expression or a variable that is defined by the spreadsheet software, and thus, it is possible to simply create the data file, compared to the case of creating the data file with robotic process automation (RPA) software. In addition, by using a copy function of the spreadsheet software, it is also possible to simply create a similar data file.

The patient health record information generation unit 113 reads out the simulated patient information stored in the server storage unit 102, and generates the patient health record information, based on the simulated patient information. In addition, the patient health record information generation unit 113 reads out the simulated patient information adequate for a display condition set by the display condition setting unit 114 described below from the server storage unit 102, and generates the patient health record information, based on the simulated patient information. Further, in a case where the display condition setting unit 114 sets a date and time different from a date and time of the date and time information included in the patient simulated information as the display condition, the patient health record information generation unit 113 generates the patient health record information using such a new date and time as a display date and time. In addition, the patient health record information generation unit 113 stores the generated patient health record information in the simulated patient information database 121 in association with learner information.

The patient health record information, for example, indicates information including information relevant to a patient placement location (for example, information relevant to a hospital ward such as a general hospital ward or a recuperation hospital ward, a hospital room (number), a hospital bed (number) (a bed number), or the like, hereinafter, may be referred to as "patient placement information"), patient basic information (for example, information relevant to a full name, an age, an address, the type of insurance, a blood type, a disorder, a disease, anamnesis, or the like), information relevant to a medical record (course) (for example, information relevant to a finding of a medical doctor, a nursing record, a medical examination article, a comfort disorder, or the like), information relevant to a temperature check table, information relevant to medication, information relevant to injection, information relevant to a general instruction, information relevant to an examination result (for example, a blood examination, a blood gas examination, a pathological examination, an image examination such as X-ray/CT/MR/endoscope, an electrocardiogram examination, a brain wave examination, an ultrasonic examination, an angiographic examination, and the like), information relevant to an examination order history, information relevant to nursing support (a nursing plan) (for example, information relevant to the intake of meal, a meal intake ratio of staple food/supernumerary food/between-meal snacks, the appetite, or the like of the simulated patient), document information (for example, a written informed consent for a surgery/anesthesia/treatment/examination, a familial diagram representing a familial relationship of the simulated patient, and the like), and the like. In addition, in a case where the date and time information is included in the simulated patient information, the patient health record information may include the date and time information.

The display condition setting unit 114 sets and changes the display condition of the patient health record information displayed on the learner terminal 30. Accordingly, the administrator is capable of freely setting and changing the contents of the patient health record information displayed on the learner terminal 30, and it is possible to make the electronic health record system of this embodiment freely adequate for the design of the exercise or the practice. For example, by setting the type of simulated patient, it is possible to perform the exercise and the practice according to various case histories or the like for the learner. Note that, a change in the display condition by the display condition setting unit 14 indicates a change between display and non-display of arbitrary information included in the patient health record information. Accordingly, the change does not indicate to change and edit the patient health record information itself.

In addition, by setting a hospital admission date or a hospital discharge date of the simulated patient, it is possible to perform the practice and the exercise in accordance with a practice/exercise start date and time of the learner. Here, the hospital admission date and the hospital discharge date may be set to a date and time different from the date and time of the virtually set date and time information included in the simulated patient information. Further, by setting a hospital admission course date and time of the simulated patient, it is possible to display the patient health record information overtime. Accordingly, it is possible to display the learner that the patient health record information is being added overtime. In addition, by setting a display end date and time of the patient health record information, it is possible to display the patient health record information according to a learning progress of the learner.

The reception unit 115 and the transmission unit 116 are means for receiving various information pieces transmitted from the learner terminal 30 and the administrator terminal 40.

The transmission unit 116 is means for transmitting various information pieces stored in the server storage unit 102, for example, the simulated patient information, the learner information, administrator information, and the like, in accordance with a request from the learner terminal 30 and the administrator terminal 40.

The image data processing unit 117 is means for enabling the upload of the image data from the administrator terminal 40. More specifically, the image data processing unit 117 receives image data in which the examination result or the like is described, which is transmitted from the administrator terminal 40, and stores the image data in the simulated patient information database 121 in association with the simulated patient information. In addition, the image data processing unit 117 generates a web page displaying the uploaded image data, and displays the web page on the learner terminal 30 and/or the administrator terminal 40.

The data file editing unit 118 is means for editing the data file imported by the data file acquisition unit 112. Specifically, the data file editing unit 118 is capable of copying at least a part of the simulated patient information in the imported data file. In addition, the data file editing unit 118 is also capable of editing and setting whether to display the information relevant to the nursing support (the nursing plan) and the information relevant to the examination result such as an examination reference value of various examinations on the learner terminal 30.

The patient health record information editing unit 119 is means for editing the patient health record information from the administrator terminal 40. Accordingly, it is possible to freely edit the contents of the patient health record information displayed on the learner terminal 30, in accordance with the progress of the exercise or the practice, the degree of learning of the learner, or the like. Information that can be edited by the patient health record information editing unit 119 is not particularly limited insofar as the information is the patient health record information, and can be arbitrarily set. Here, the patient health record information editing unit 119 is means for correcting information that is displayed as the patient health record information, and is not capable of adding information that is not displayed as the patient health record information, adding and deleting display items, and changing the date and time information.

In the server storage unit 102, for example, a plurality of storage areas are defined, and the server storage unit includes at least a simulated patient information database 121, a learner information database 122, and an administrator information database 123. As such a server storage unit 102, a storage medium such as a hard disk for storing data or a program for storage can be used.

The simulated patient information database 121 stores the simulated patient information (including the simulated patient number) imported by the data file acquisition unit 112. In addition, the simulated patient information database 121 stores the virtually set patient placement information. As described above, the virtually set patient placement information, for example, includes the hospital ward such as a general hospital ward or a recuperation hospital ward, the hospital room (number), the hospital bed (number) (the bed number), and the like. In addition, the patient placement information is stored in the simulated patient information database 121 in association with the simulated patient information. Further, the image data of the document information that is uploaded from the from the administrator terminal 40 and is imported by the image data processing unit 117 is also stored. Note that, the simulated patient information may include the simulated patient information that is directly input by the administrator terminal 40 or the like, in addition to the information imported by the data file acquisition unit 112.

The learner information database 122 stores the learner information of the learner. The learner information, for example, includes account information of the learner, more specifically, the full name or the name of the learner, location information indicating a location, such as an address of the learner, a connection password for the connection of the learner terminal 30 to the electronic health record server 10, an e-mail address of the learner, information relevant to payment (for example, credit card information or the like), and the like. In addition, the learner information may include a terminal identifier for identifying the learner terminal 30. The terminal identifier is not particularly limited, and for example, a number, a character, a symbol, or a combination thereof can be used as the identifier.

The administrator information database 123 stores the administrator information of the administrator. The administrator information, for example, include account information of the administrator, more specifically, the full name or the name of the administrator, location information indicating a location, such as an address of the administrator, a connection password for the connection of the administrator terminal 40 to the electronic health record server 10, the e-mail address of the learner, and the information relevant to the payment (for example, the credit card information or the like), and the like. In addition, the administrator information may include a terminal identifier for identifying the administrator terminal 40, and a facility identifier for identifying a facility to which the administrator belongs. The terminal identifier and the facility identifier are not particularly limited, and for example, a number, a character, a symbol, or a combination thereof can be used as the identifier.

The interface unit 103 enables input/output by the generation of the web page, and transmits the web page on the network 20 to be displayed on the learner terminal 30 and the administrator terminal 40 with a web browser. More specifically, the interface unit is realized by a common gateway interface (CGI) script. CGI is an interface that activates the corresponding program on a WWW server side, that is, the CGI script with respect to a request transmitted from a browser of a client, and returns a result obtained by the program to the client side. The CGI script is stored in the memory 203. When transmitting a HTML document to the learner terminal 30 or the administrator terminal 40 from the electronic health record server 10 connected to the internet, a hypertext transport protocol (HTTP) is adopted as a protocol.

(Operation of Educational Electronic Health Record System)

Next, the operation of the electronic health record system of this embodiment will be described with reference to the drawings. Note that, various operations of the electronic health record system are realized by the electronic health record program that is provided in the server storage unit 102 of the electronic health record server 10 to realize the function of each constituent such as the registration reception unit 111 of the server control unit 101. Then, the electronic health record program includes a code for performing various operations described below, and implements the function of each constituent.

[Initial Registration Processing]

Figure 5:
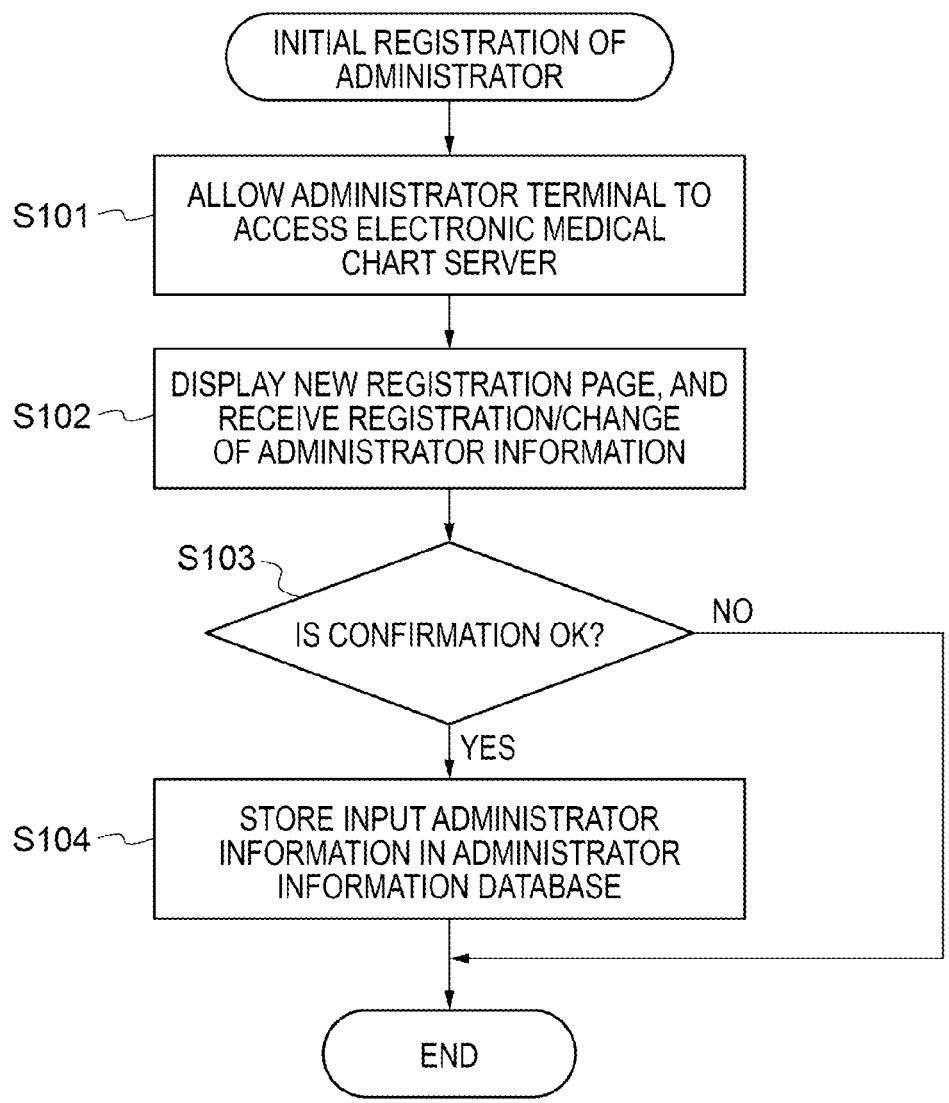
FIG. 5 is a flowchart illustrating a flow of initial registration processing using the educational electronic health record system according to the embodiment of the present invention.

First, initial registration processing of the administrator will be described based on FIG. 5. FIG. 5 is a flowchart illustrating the flow of the initial registration processing of the administrator. As illustrated in the same drawing, the administrator uses the electronic health record system of this embodiment, and thus, first, accesses the electronic health record server 10 from the administrator terminal 40 through the network 20 and performs initial registration. In a case where the administrator accesses the electronic health record server 10 from the administrator terminal 40 through the network 20 (S101), the registration reception unit 111 of the electronic health record server 10 transmits the data of the HTML document for displaying a home page that provides an electronic health record service to the administrator terminal 40. Accordingly, a new registration page for the administrator is displayed on a display or the like of the administrator terminal 40.

In the new registration page of the administrator, the administrator inputs entry relevant to the administrator information by using input means such as a keyboard or a mouse that is provided in the administrator terminal 40 (S102). In addition, for example, a function of displaying a confirmation screen relevant to the input entry from the administrator terminal 40 may be added to the new registration page of the administrator. Accordingly, after input, the registration reception unit 111 is capable of transmitting the confirmation screen of the input entry to the administrator terminal 40 (S103). The administrator confirms the input entry, and as a result thereof, in a case where there is no input leakage, error, or the like, the administrator information is transmitted to the electronic health record server 10 by selecting a transmission button. In a case where the reception unit 115 receives the administrator information, the registration reception unit 111 receives the newly registered administrator information, imparts an administrator identifier to the administrator information, and then, stores the administrator information in the administrator information database 123 (S104).

[Data File Importing Processing]

Figure 6:
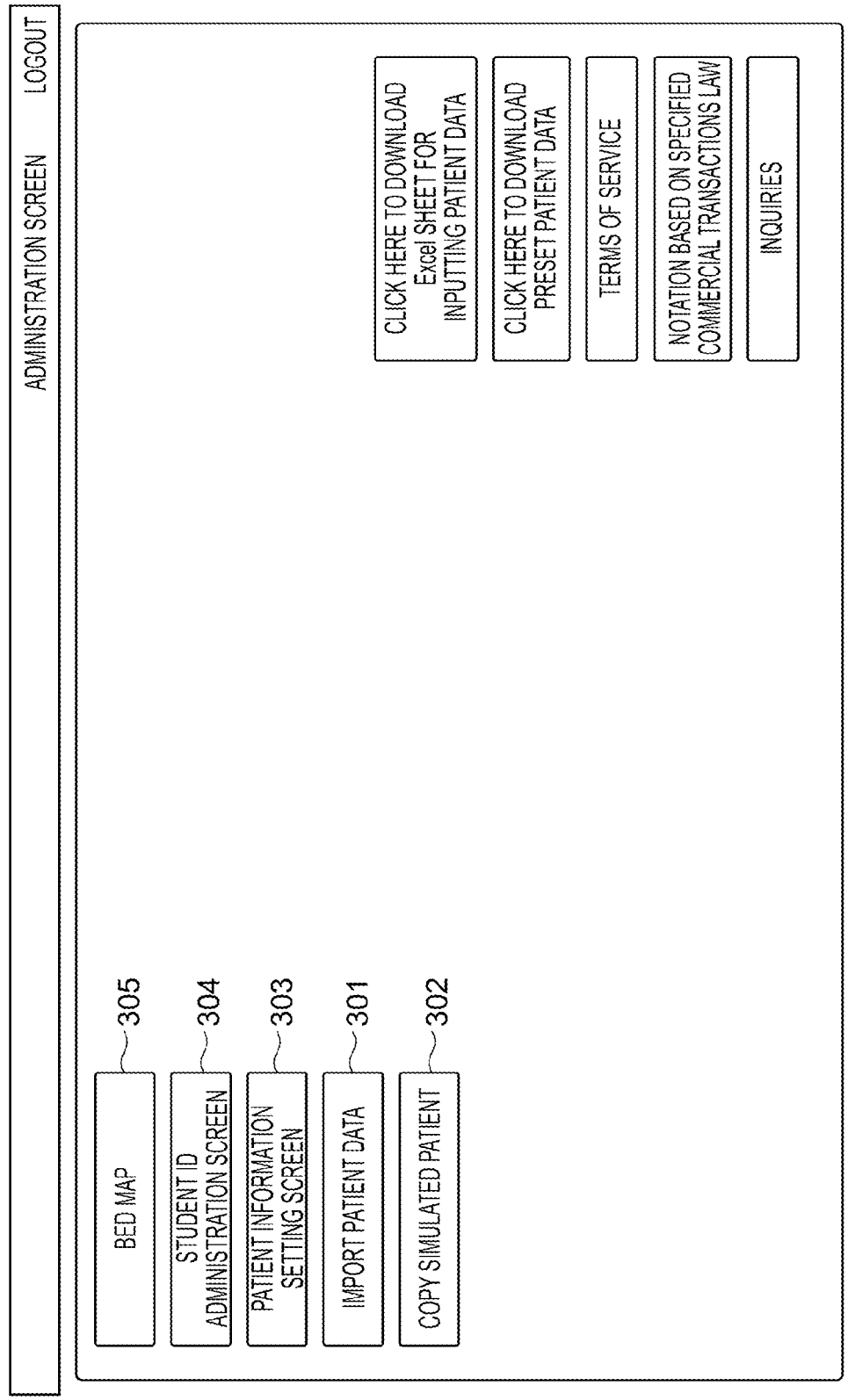
FIG. 6 is an explanatory diagram illustrating an administrator screen page displayed on an administrator terminal of a registered administrator.

Next, data file importing processing of the administrator terminal 40 will be described based on FIG. 6. FIG. 7(a) and FIG. 7(b). FIG. 6 is an explanatory diagram illustrating an administrator screen page 209 displayed on the administrator terminal 40 of the registered administrator. FIG. 7(a) is an explanatory diagram illustrating an upload reception screen page of the data file, and FIG. 7(b) is an explanatory diagram illustrating the upload completion screen page after upload.

The data file importing processing is processing for storing the simulated patient information in the simulated patient information database 121 of the electronic health record server 10. Accordingly, it is possible to generate the patient health record information displayed on the learner terminal 30.

First, in a case where the administrator accesses the electronic health record server 10 from the administrator terminal 40 through the network 20, the registration reception unit 111 of the electronic health record server 10 displays a login page of the registered administrator on the display or the like of the administrator terminal 40. In a case where the administrator inputs the connection password, the administrator identifier, and the facility identifier by using the input means such as a keyboard or a mouse that is provided in the administrator terminal 40, in the login page of the administrator, the administrator screen page 209 as illustrated in FIG. 6 is displayed.

The administrator screen page 209, for example, includes a bed map display page, a learner administration page (a learner registration reception page, a simulated patient setting page, or the like), simulated patient information setting page, an upload reception screen page 213 of the data file, and a simulated patient information editing page 214. Note that, other pages may be added to the administrator screen page 209, in accordance with the function or the like.

In the administrator terminal 40, in a case where a patient data import button 301 on the administrator screen page 209 is selected, the data file acquisition unit 112 receives an upload request for the data file. Further, as illustrated in FIG. 7(a), the data file acquisition unit 112 displays an upload reception screen 213 on the administrator terminal 40. Subsequently, the data file is uploaded to the electronic health record server 10 by the administrator terminal 40. In a case where the electronic health record server 10 receives the data file from the administrator terminal 40, the data file acquisition unit 112 stores the data file in the simulated patient information database 121. Further, as illustrated in FIG. 7(b), the data file acquisition unit 112 displays an upload completion screen 214 displaying that the success of the import of the data file on the administrator terminal 40. Here, in a case where the simulated patient number corresponding to each simulated patient is not included in the data file, the data file acquisition unit 112 imparts the simulated patient number corresponding to the simulated patient. As described above, the data file importing processing of the electronic health record server 10 is ended.

[Data File Editing Processing]

Next, data file editing processing will be described based on FIG. 8(a) and FIG. 8(b). FIG. 8(a) is an explanatory diagram illustrating a simulated patient information copy screen page for performing simulated patient information copy processing, and FIG. 8(b) is an explanatory diagram illustrating a simulated patient information copy completion screen page.

The data file of the simulated patient information stored in the simulated patient information database 121 can be edited by the data file editing unit 118. Specifically, the simulated patient information copy processing can be performed.

The simulated patient information copy processing is processing for copying at least one simulated patient information piece stored in the simulated patient information database 121. More specifically, the simulated patient information copy processing is executed as follows. That is, first, in the administrator terminal 40, in a case where a simulated patient copy button 302 on the administrator screen page 209 is selected, the data file editing unit 118 receives a copy request for the simulated patient information. Further, as illustrated in FIG. 8(a), the data file editing unit 118 displays a simulated patient information copy screen page 215 on the administrator terminal 40. A list of the simulated patient information stored in the simulated patient information database 121 is displayed on the simulated patient information copy screen page 215, and the simulated patient information to be a copy target can be selected by the input means of the administrator terminal 40.

Subsequently, at least one simulated patient information piece to be copied is selected by the input means of the administrator terminal 40, and "Copy Checked Data" is selected. Accordingly, the data file editing unit 118 receives a copy request for the selected simulated patient information, newly imparts the simulated patient number, and then, copies the simulated patient information, and stores the copied information in the simulated patient information database 121. In a case where new simulated patient information is stored in the simulated patient information database 121, the data file editing unit 118 displays a simulated patient information copy completion screen page 216 displaying a list of the new simulated patient information on the administrator terminal 40. The simulated patient information which is copied and to which the simulated patient number is newly imparted is also displayed on the simulated patient information copy completion screen page 216. As described above, the simulated patient information copy processing is ended.

[Learner Registration Processing]

Figure 9:
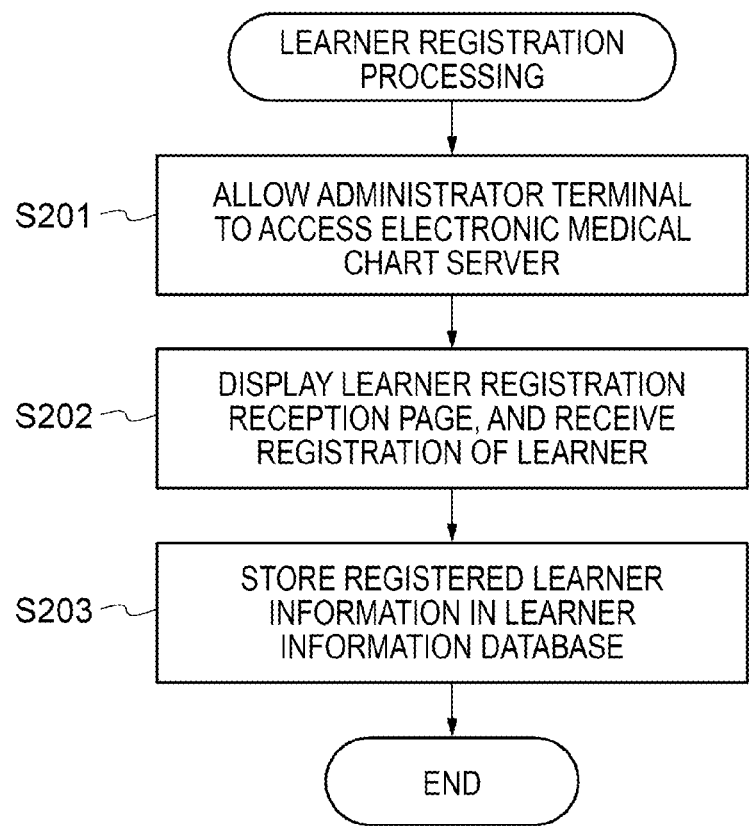
FIG. 9 is a flowchart illustrating a flow of learner registration processing using the educational electronic health record system according to the embodiment of the present invention.
Figure 10A:
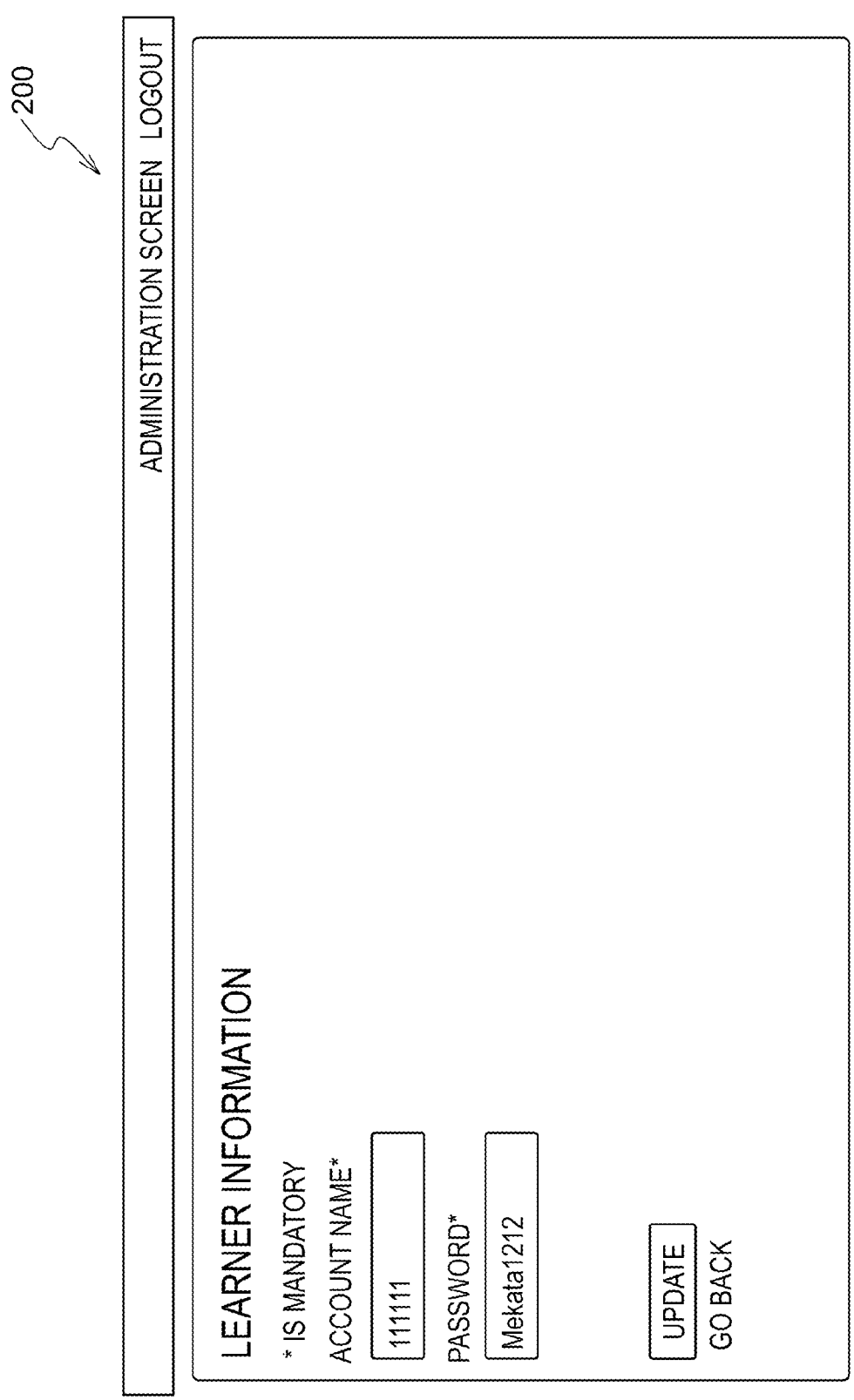
FIG. 10(a) is an explanatory diagram illustrating a learner registration reception page.

Next, learner registration processing of the administrator will be described based on FIG. 9, FIG. 10(a), and FIG. 10(b). FIG. 9 is a flowchart illustrating the flow of the learner registration processing of the administrator terminal 40. FIG. 10(a) is an explanatory diagram illustrating a learner registration reception page 200, and FIG. 10(b) is an explanatory diagram illustrating a learner administration page indicating a registered learner.

As illustrated in FIG. 9, the administrator accesses the electronic health record server 10 from the administrator terminal 40 through the network 20, and in a case where a student ID administration screen button 304 on the administrator screen page 209 is selected, the registration reception unit 111 receives a learner registration request (S201). Subsequently, the registration reception unit 111 transmits the data of the HTML document for displaying the learner registration reception page 200 to the administrator terminal 40. Accordingly, the learner registration reception page 200 is displayed on the display or the like of the administrator terminal 40. Note that, other pages may be added to the learner registration reception page 200, in accordance with the function or the like.

As illustrated in FIG. 10(a), in the learner registration reception page 200, the administrator inputs entry relevant to the learner information by using input means such as a keyboard or a mouse that is provided in the administrator terminal 40 (S202). Examples of the entry relevant to the learner information include an account name of the learner, the connection password for the connection to the electronic health record server 10 from the learner terminal 30, and the like.

In a case where the learner information is transmitted to the electronic health record server 10 and is received by the reception unit 115, the registration reception unit 111 receives the learner information, imparts the learner identifier, and then, stores the learner information including the learner identifier in the learner information database 122 (S203). Further, in a case where the learner information is stored in the learner information database 122, as illustrated in FIG. 10(b), the registration reception unit 111 transmits a learner administration page 201 indicating new learner registered entry to the administrator terminal 40. As described above, the learner registration processing is ended.

[Setting Processing of Display Condition of Patient Health Record Information]

Setting processing of the display condition of the patient health record information by the administrator will be described.

Figure 11:
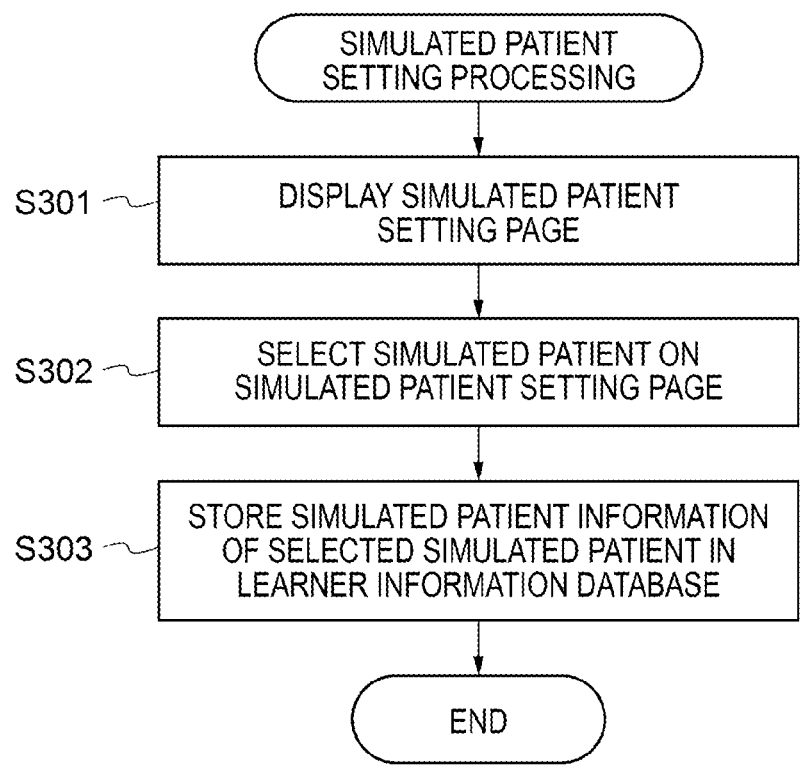
FIG. 11 is a flowchart illustrating a flow of simulated patient setting processing of the administrator using the educational electronic health record system according to the embodiment of the present invention.

First, simulated patient setting processing will be described based on FIG. 11 and FIG. 12. FIG. 11 is a flowchart illustrating the flow of the simulated patient setting processing of the administrator. FIG. 12 is an explanatory diagram illustrating a simulated patient setting page 202 for setting the simulated patient displayed to the registered learner.

The simulated patient setting processing is processing for setting which simulated patient information is displayed to the registered learner as the patient health record information. That is, in a case where a setting request for the simulated patient is received from the administrator terminal 40, the display condition setting unit 114 displays the simulated patient setting page 202 for setting the simulated patient on the administrator terminal 40 (refer to S301 and FIG. 12). Further, the simulated patient information stored in the simulated patient information database 121 is called, and simulated patient candidates to be selected are displayed on the simulated patient setting page 202.

In a case where the simulated patient setting page 202 is displayed on the administrator terminal 40, the administrator selects the simulated patient from the simulated patient candidates that are displayed on the simulated patient setting page 202, by using the input means such as a keyboard or a mouse that is provided in the administrator terminal 40 (S302). At least one simulated patient can be selected. In a case where the simulated patient is selected, and an update button displayed on the simulated patient setting page 202 is selected, the display condition setting unit 114 receives the selection of the simulated patient, and stores the simulated patient information of the selected simulated patient in the simulated patient information database 121 in association with the learner information (S303). As described above, the simulated patient setting processing is ended.

Figure 13:
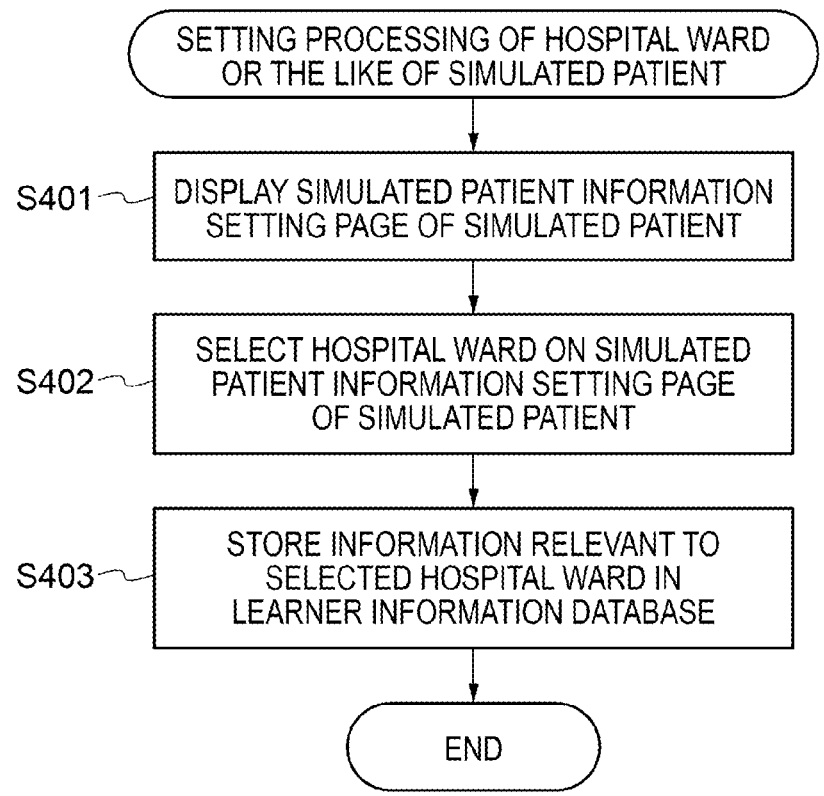
FIG. 13 is a flowchart illustrating a flow of setting processing of a hospital ward or the like of the simulated patient using the educational electronic health record system according to the embodiment of the present invention.

Next, setting processing of a hospital ward or the like of the selected simulated patient will be described based on FIG. 13 and FIG. 14. FIG. 13 is a flowchart of the flow of the setting processing of the hospital ward or the like of the selected simulated patient. FIG. 14 is an explanatory diagram illustrating a simulated patient information setting page 203 for setting the selected simulated patient information.

The setting processing of the hospital ward is processing for virtually setting in which hospital ward the selected simulated patient is hospitalized. That is, in a case where the administrator accesses the electronic health record server 10 from the administrator terminal 40 through the network 20, and a patient information setting screen button 303 on the administrator screen page 209 is selected in the administrator terminal 40, the display condition setting unit 114 receives a setting request for the simulated patient information. Further, the display condition setting unit 114 displays the simulated patient information setting page 203 for setting the hospital ward on the administrator terminal 40 (refer to S401 and FIG. 13).

In a case where the simulated patient information setting page 203 is displayed on the administrator terminal 40, in the simulated patient information setting page 203, the administrator performs the setting of the virtually set hospital ward or the like for each simulated patient, by using the input means such as a keyboard or a mouse that is provided in the administrator terminal 40 (S402). As illustrated in FIG. 14, the setting of the hospital ward or the like, for example, is performed by setting the floor number of an admission hospital bed and the admission hospital bed (the hospital bed (bed) number or the hospital room number). In a case where the hospital ward is selected for each selected simulated patient, and the update button that is displayed on the simulated patient information setting page 203 is selected, the display condition setting unit 114 receives the selection of the hospital ward. Further, the display condition setting unit 114 stores the selected hospital ward together with the simulated patient information of the selected simulated patient in the simulated patient information database 121 as the patient placement information, in association with the learner information (S403).

In a case where the patient placement information is stored in the simulated patient information database 121, the patient health record information generation unit 113 displays a bed map display page 204 on the learner terminal 30 or the administrator terminal 40, based on the patient placement information, and the simulated patient information and the learner information associated with the patient placement information (refer to FIG. 15). As illustrated in FIG. 15, the bed map information is displayed on the bed map display page 204. Here, the bed map information indicates information representing a simulated patient placement location in the virtual hospital ward. In addition, the bed map display page 204 may be displayed on the learner terminal 30. As described above, the setting processing of the hospital ward or the like of the simulated patient is ended. Note that, FIG. 15 is an explanatory diagram illustrating the bed map display page 204 displaying the information relevant to the patient placement location in the hospital ward.

Figure 16:
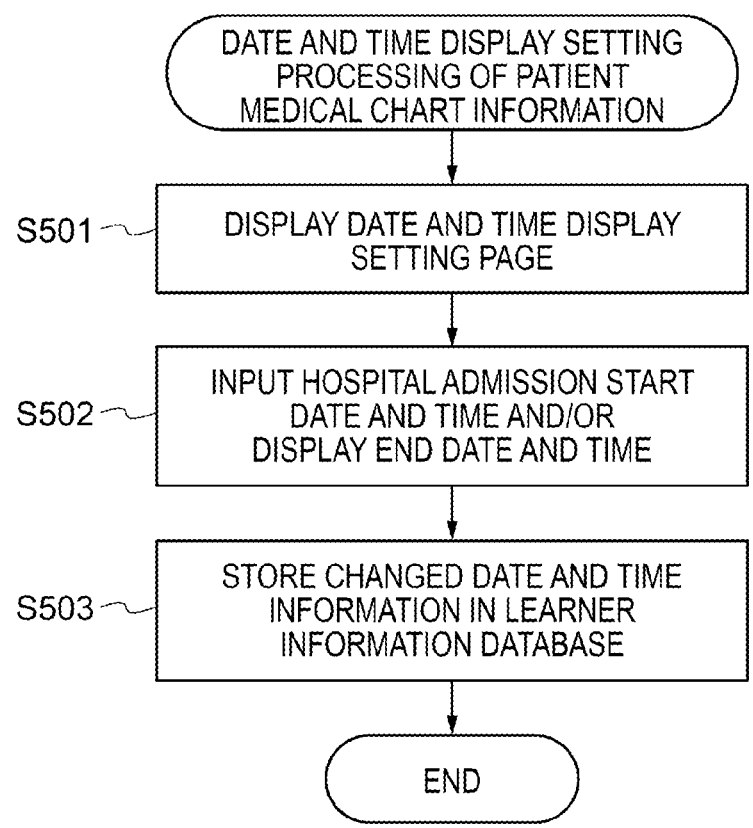
FIG. 16 is a flowchart illustrating a flow of date and time display setting processing of patient health record information using the educational electronic health record system according to the embodiment of the present invention.
Figure 17B:
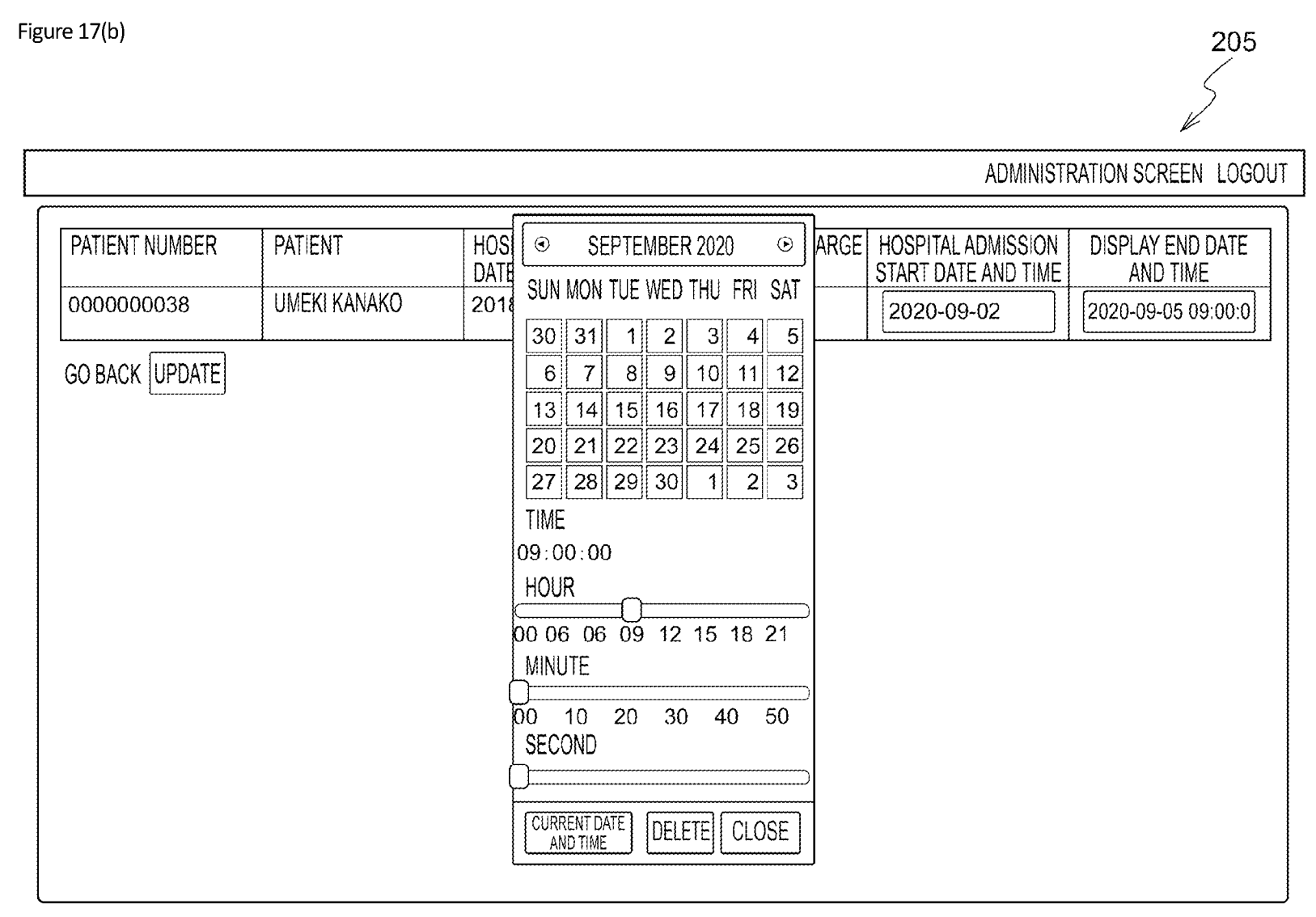

Subsequently, date and time display setting processing of the patient health record information will be described based on FIG. 16, FIG. 17(a) and FIG. 17(b). FIG. 16 is a flowchart illustrating the flow of the date and time display setting processing of the patient health record information. FIG. 17(a) and FIG. 17(b) are explanatory diagrams illustrating a date and time display setting page 205 for changing date and time display of the patient health record information.

The date and time display setting processing of the patient health record information is processing for virtually changing and setting the hospital admission date of the simulated patient. That is, as illustrated in FIG. 16, in a case where the administrator terminal 40 accesses the electronic health record server 10 through the network 20, the display condition setting unit 114 displays the date and time display setting page 205 for change-setting the date and time display of the simulated patient information of the selected simulated patient on the administrator terminal 40 (S501).

As illustrated in FIG. 17(a), the hospital admission date and time and the hospital discharge date and time of the simulated patient are displayed on the date and time display setting page 205 before change-setting, based on the initial date and time information included in the simulated patient information. Then, in the case of changing the hospital admission date and time and the hospital discharge date and time of the simulated patient, for example, corresponding to a practice start date of the learner, a new date is input to a hospital admission start date column and/or a display end date column by using the input means such as a keyboard or a mouse that is provided in the administrator terminal 40 (S502). Note that, in this embodiment, time can also be set in the display end date column, in addition to the date (refer to FIG. 17(b)). The time of the display end date can be set, and thus, for example, the patient health record information can be updated overtime in real time during the practice of the learner, and a practice/exercise effect is further improved.

In a case where the new date is input to the hospital admission start date column and/or the display end date column, and an update button that is displayed on the date and time display setting page 205 is selected, the display condition setting unit 114 receives a change request for the date and time information. Further, the display condition setting unit 114 stores the new date together with the simulated patient information of the selected simulated patient in the simulated patient information database 121 as the date and time information displayed on the learner terminal 30, in association with the learner information (S503). As described above, the date and time display setting processing of the patient health record information is ended.

Figure 18:
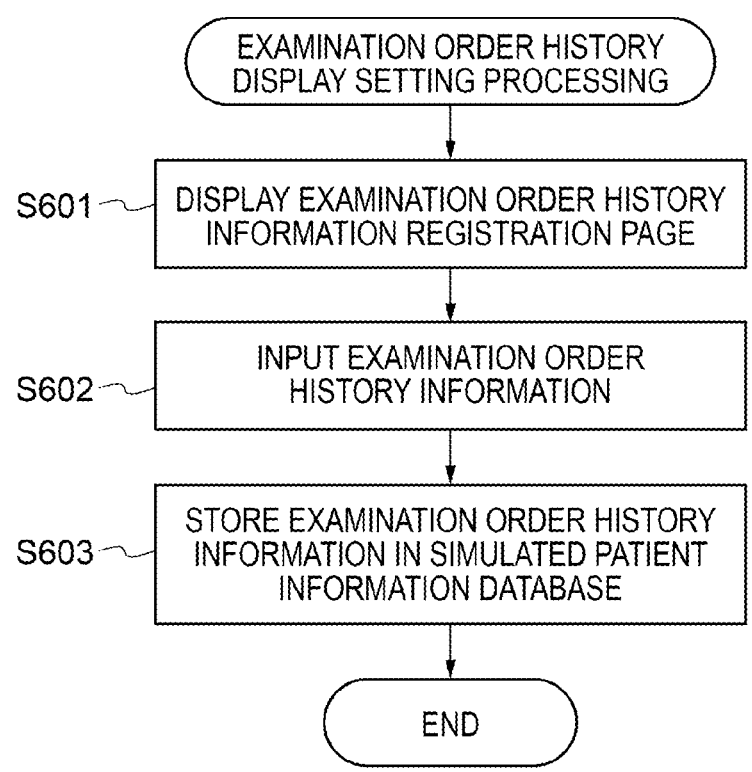
FIG. 18 is a flowchart illustrating a flow of examination order history display setting processing using the educational electronic health record system according to the embodiment of the present invention.

Next, examination order history display setting processing will be described based on FIG. 18. FIG. 19(a) and FIG. 19(b). FIG. 18 is a flowchart illustrating the flow of the examination order history display setting processing. FIG. 19 (a) is an explanatory diagram illustrating an examination order history information registration page 206 for registering the information relevant to the examination order history (hereinafter, referred to as "examination order history information"), and FIG. 19 (b) is an explanatory diagram illustrating a document information display page 207 displaying image data in which various examination results are described.

As illustrated in FIG. 19(a) and FIG. 19(b), in a case where the administrator terminal 40 accesses the electronic health record server 10 through the network 20, the display condition setting unit 114 displays the examination order history information registration page 206 for setting examination order history display on the administrator terminal 40 (S601).

As illustrated in FIG. 19(a), the examination order history information such as an examination type such as an ultrasonic examination, an order date on which the examination is ordered, examination order time, and a requested diagnosis and treatment department from which the examination is requested is input on the examination order history information registration page 206, by using the input means such as a keyboard or a mouse that is provided in the administrator terminal 40 (S602).

In a case where the examination order history information is input, and an update button that is displayed on the examination order history information registration page 206 is selected, the display condition setting unit 114 receives the setting of the examination order history information. Further, the display condition setting unit 114 stores the examination order history information together with the simulated patient information of the selected simulated patient in the simulated patient information database 121 as the examination order history information displayed on the learner terminal 30, in association with the learner information (S603). As described above, the examination order history display setting processing is ended.

Note that, the image data in which various examination results are described can also be uploaded to the electronic health record server 10 on the examination order history information registration page 206. That is, in a case where the image data is received from the administrator terminal 40, the image data processing unit 117 stores the image data in the simulated patient information database 121, in association with the simulated patient information. Further, the image data processing unit 117 generates the document information display page 207 displaying the uploaded image data to be displayed on the administrator terminal 40.

In addition, in the setting processing of the display condition of the patient health record information by the administrator, the document information (for example, the written informed consent relevant to the surgery/anesthesia/treatment/examination, a familial diagram representing the familial relationship of the simulated patient, or the like) may be displayed. In this case, the document information is uploaded to the electronic health record server 10 as the image data. That is, in a case where the image data is received from the administrator terminal 40, the image data processing unit 117 stores the image data in the simulated patient information database 121, in association with the simulated patient information. Further, the image data processing unit 117 generates the web page displaying the uploaded image data to be displayed on the administrator terminal 40. The display condition setting unit 114 stores the document information stored in the simulated patient information database 121 together with the simulated patient information of the selected simulated patient in the simulated patient information database 121 as the document information displayed on the learner terminal 30, in association with the learner information.

Further, in the setting processing of the display condition of the patient health record information by the administrator, it is also possible to set the display or non-display of the nursing plan, and the display or non-display of the examination reference value. Here, the examination reference value indicates a reference value in various examinations such as a blood examination. In the simulated patient information setting page 203 illustrated in FIG. 14, such setting is performed by setting the display/non-display of the nursing plan, and the display/non-display of the examination reference value.

In a case where the display or non-display of the nursing plan and the examination reference value is selected for each selected simulated patient, and the update button that is displayed on the simulated patient information setting page 203 is selected, the display condition setting unit 114 receives the selection of the display or non-display of the nursing plan and the examination reference value. Further, the display condition setting unit 114 stores the display or non-display of the nursing plan and the examination reference value together with the simulated patient information of the selected simulated patient in the simulated patient information database 121 as the information relevant to the nursing support (the nursing plan) and the information relevant to the examination result (hereinafter, referred to as the "nursing support information or the like"), respectively, in association with the learner information.

In a case where the nursing support information or the like is stored in the simulated patient information database 121, the patient health record information generation unit 113 displays an electronic health record display page on the administrator terminal 40, based on the nursing support information or the like, and the simulated patient information and the learner information associated with the nursing support information or the like.

Figure 20:
FIG. 20 is an explanatory diagram illustrating an electronic health record display page displayed on the learner terminal.

As described above, in a case where the setting processing of the display condition of the patient health record information by the administrator is ended, the electronic health record server 10 is capable of displaying an electronic health record display page 208 as illustrated in FIG. 20 on the learner terminal 30 of the learner, based on the display condition set by the administrator. That is, in a case where the learner accesses the electronic health record server 10 by the learner terminal 30 through the network 20, the patient health record information generation unit 113 calls the simulated patient information adequate for the display condition set/changed by the display condition setting unit 114 from the simulated patient information database 121, and generates the simulated patient information as the patient health record information. Further, the electronic health record display page 208 on which the generated patient health record information is described can be displayed on the display unit 34 such as a display of the learner terminal 30. Various documents or reports such as the medical record (a course table), the temperature check table, medication (instruction), injection (instruction), a general instruction, the examination result, an order history, the nursing support, and a surgical written informed consent can also be browsed on the electronic health record display page 208, in addition to the patient basic information. In addition, the learner is also capable of browsing the bed map display page 204. Note that, FIG. 20 is an explanatory diagram illustrating the electronic health record display page 208 that is displayed on the learner terminal 30.

[Editing Processing of Display Contents of Patient Health Record Information]

Figure 21:
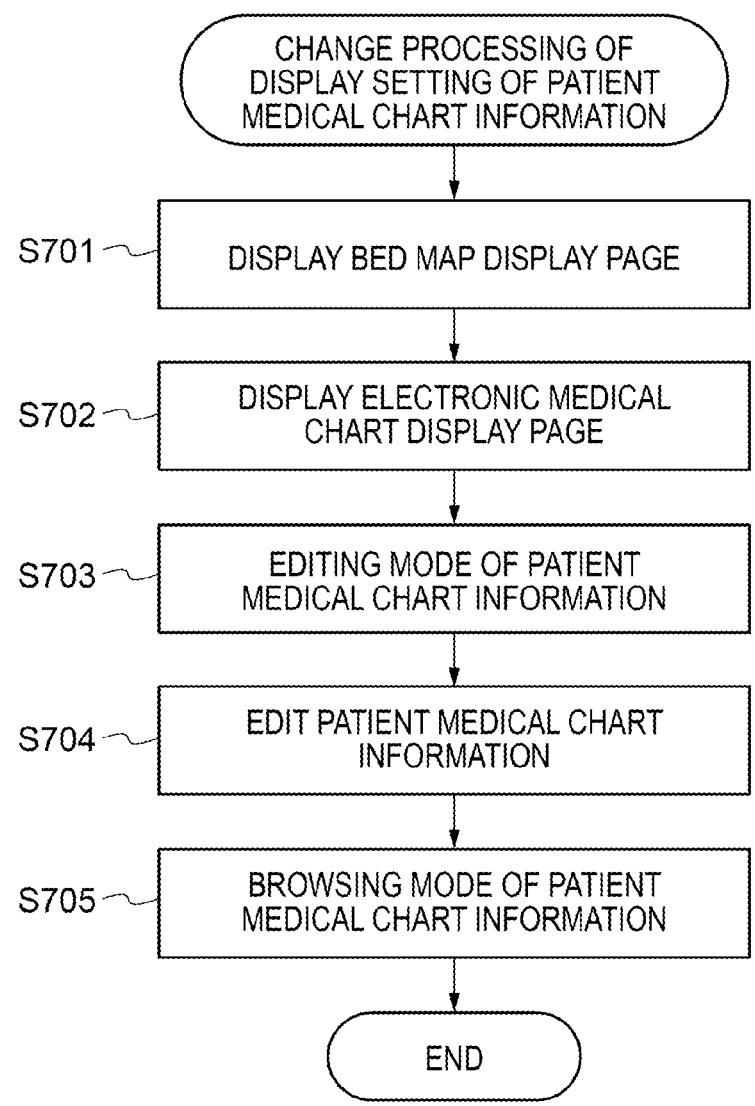
FIG. 21 is a flowchart illustrating a flow of change processing of a display condition of the patient health record information by the administrator terminal using the educational electronic health record system according to the embodiment of the present invention.

Next, editing processing of the display condition of the patient health record information by the administrator will be described based on FIG. 21 and FIG. 22. FIG. 21 is a flowchart illustrating the flow of editing processing of the display contents of the patient health record information by the administrator terminal using the educational electronic health record system according to this embodiment. FIG. 22 is an explanatory diagram illustrating an electronic health record editing page 211 that is displayed on the administrator terminal 40.

The editing processing of the display contents of the patient health record information is processing for the administrator to edit the display contents of the patient health record information displayed on the learner terminal 30. Accordingly, in this embodiment, the contents of the patient health record information displayed on the learner terminal 30 can be freely changed in accordance with the progress or the learning contents of the exercise or the practice, the degree of learning of the learner, or the like.

First, in a case where the administrator accesses the electronic health record server 10 from the administrator terminal 40 through the network 20, and a bed map button 305 of the administrator screen page 209 is selected in the administrator terminal 40, the patient health record information generation unit 113 displays the bed map display page 204 on the display or the like of the administrator terminal 40 (refer to S701, FIG. 15, and FIG. 21).

Bed map information relevant to the simulated patient is displayed on the bed map display page 204, and in a case where an arbitrary simulated patient is selected from the bed map information by using the input means of the administrator terminal 40, the patient health record information generation unit 113 receives a display request for the electronic health record display page displaying an electronic health record relevant to the selected simulated patient. Further, the patient health record information generation unit 113 displays the electronic health record display page on the display or the like of the administrator terminal 40 (refer to S702 and FIG. 21).

Subsequently, a data editing mode button 210 that is displayed on the electronic health record display page is selected by using the input means such as a mouse in the administrator terminal 40. The data editing mode button 210 is a button for the transition to an editing mode for editing an arbitrary display item in the electronic health record display page. In a case where the data editing mode button 210 is selected, the patient health record information editing unit 119 receives a request for the transition to the editing mode of the patient health record information, and displays the electronic health record editing page 211 illustrated in FIG. 22 on the administrator terminal 40 (S703).

In a case where the electronic health record editing page 211 is displayed on the administrator terminal 40, the patient health record information can be edited by using the input means of the administrator terminal 40 (S704). That is, in a case where the arbitrary patient health record information is edited by the administrator terminal 40, and an update button 212 is selected, new patient health record information that is input is transmitted to the electronic health record server 10. Further, in a case where the new patient health record information is received by the reception unit 115 of the electronic health record server 10, the patient health record information editing unit 119 updates the simulated patient information stored in the simulated patient information database 121, based on the new patient health record information, and stores again the simulated patient information in the simulated patient information database 121. In a case where the simulated patient information is updated, the patient health record information generation unit 113 reads out the simulated patient information stored in the simulated patient information database 121, and generates the patient health record information, based on the simulated patient information. Alternatively, the patient health record information generation unit 113 reads out the simulated patient information adequate for the display condition set by the display condition setting unit 114 from the simulated patient information database 121, and generates new patient health record information, based on the simulated patient information. Further, the patient health record information generation unit 113 displays the electronic health record display page on which the new patient health record information is reflected on the administrator terminal 40 (S705). In this case, the page that is displayed on the administrator terminal 40 is not the electronic health record editing page 211 but the electronic health record display page 208 in a browsing mode.

As described above, in a case where the editing processing of the display contents of the patient health record information by the administrator terminal 40 is ended, the electronic health record server 10 is capable of displaying the electronic health record display page after change on the learner terminal 30, based on the display condition changed by the administrator terminal 40.

This embodiment exemplifies the educational electronic health record system and the educational electronic health record program for embodying the technical idea of the present invention, and is not intended to limit the present invention to the embodiment. Accordingly, the present invention can be equally applied to an educational electronic health record system and an educational electronic health record program of other embodiments included in the claims. For example, the form of function distribution of the learner terminal, the administrator terminal, and the educational electronic health record server of the educational electronic health record system and the educational electronic health record program exemplified in this embodiment is not limited to the above case, and functional or physical distribution or integration in arbitrary unit can be made within a range where the same effect or function can be obtained.

REFERENCE SIGNS LIST

10 . . . electronic health record server, 11 . . . CPU, 12 . . . ROM, 13 . . . RAM, 14 . . . communication control interface, 15 . . . storage device, 16 . . . input manipulation unit, 20 . . . network, 30 . . . learner terminal, 31 . . . CPU, 32 . . . ROM, 33 . . . RAM, 34 . . . display unit, 35 . . . input unit, 36 . . . communication control interface, 40 . . . administrator terminal, 101 . . . server control unit, 102 . . . server storage unit (storage unit), 103 . . . user interface unit, 111 . . . registration reception unit, 112 . . . data file acquisition unit, 113 . . . patient health record information generation unit, 114 . . . display condition setting unit, 115 . . . reception unit, 116 . . . transmission unit, 117 . . . image data processing unit, 118 . . . data file editing unit, 119 . . . patient health record information editing unit, 121 . . . simulated patient information database, 122 . . . learner information database, 123 . . . administrator information database, 200 . . . learner registration reception page, 201 . . . learner administration page, 202 . . . simulated patient setting page, 203 . . . simulated patient information setting page, 204 . . . bed map display page, 205 . . . date and time display setting page, 206 . . . examination order history information registration page, 207 . . . document information display page, 208 . . . electronic health record display page, 209 . . . administrator screen page, 210 . . . data editing mode button, 211 . . . electronic health record editing page, 212 . . . update button, 213 . . . upload reception screen page, 214 . . . upload completion screen, 215 . . . simulated patient information copy screen page, 216 . . . simulated patient information copy completion screen page, 301 . . . patient data import button, 302 . . . simulated patient copy button, 303 . . . patient information setting screen button, 304 . . . student ID administration screen button, 305 . . . bed map button

The invention claimed is:

1. An educational electronic health record system, consisting of:
a learner terminal;
an administrator terminal; and
an educational electronic health record server connected to the learner terminal and the administrator terminal through a network,
wherein the educational electronic health record server includes:
a data file acquisition unit acquiring a data file that is described in a data format of arbitrary software and includes simulated patient information, in accordance with a request from the administrator terminal;
a storage unit storing the simulated patient information of the data file acquired by the data file acquisition unit, and bed map information of a patient that is associated with at least the simulated patient information and is virtually determined;
a display condition setting unit setting a display condition of the patient health record information displayed on the learner terminal, and changing display or non-display of arbitrary information included in the patient health record information;

a patient health record information generation unit calling the simulated patient information and the bed map information of the patient each stored in the storage unit, based on the display condition set or changed by the display condition setting unit, and automatically generating patient health record information that is displayed on the learner terminal, based on the called simulated patient information, and includes the bed map information of the patient; and a patient health record information editing unit editing the patient health record information generated by the patient health record information generation unit, in accordance with a request from the administrator terminal, the display condition setting unit stores the simulated patient information that is associated with the bed map information and is of a patient selected for each learner, in the storage unit with the simulated patient information associated with leaner information of the learner, the patient health record information generation unit displays the bed map information associated with the learner information on the administrator terminal, when an arbitrary simulated patient is selected from the displayed bed map information, displays an electronic health record relevant to the selected simulated patient on the administrator terminal, and, when the patient health record information editing unit receives a request for transition to an editing mode from the administrator terminal, displays the electronic health record such that the electronic health record cannot be edited, and the patient health record information generation unit displays, based on the display condition, the bed map information associated with the learner information on the learner terminal such that the bed map information cannot be edited and, when an arbitrary simulated patient is selected from the displayed bed map information, displays an electronic health record relevant to the selected simulated patient on the learner terminal such that the electronic health record cannot be edited.

2. The educational electronic health record system according to claim 1, wherein the simulated patient information stored in the storage unit is associated with arbitrary information included in the simulated patient information and includes virtually set date and time information, the display condition setting unit sets a date and time different from a date and time included in the date and time information, and the patient health record information generation unit generates the patient health record information displayed on the learner terminal, based on the date and time set by the display condition setting unit.

3. The educational electronic health record system according to claim 1, wherein the patient health record information editing unit updates the simulated patient information stored in the storage unit, based on new patient health record information edited by the patient health record information editing unit.

4. A computer-readable educational electronic health record program for causing an educational electronic health record server connected to a learner terminal and an administrator terminal through a network to execute:

processing for acquiring a data file that is described in a data format of arbitrary software and includes simulated patient information, in accordance with a request from the administrator terminal;

processing for storing the acquired simulated patient information and bed map information of a patient that is associated with at least the simulated patient information and is virtually determined, in a storage unit of the educational electronic health record server;

processing for setting a display condition of the patient health record information displayed on the learner terminal, or changing display or non-display of arbitrary information included in the patient health record information;

processing for calling the simulated patient information and the bed map information of the patient each stored in the storage unit, based on the set or changed display condition, and automatically generating patient health record information that is displayed on the learner terminal, based on the called simulated patient information, and includes the bed map information of the patient;

processing for editing the generated patient health record information in accordance with a request from the administrator terminal;

processing for storing the simulated patient information that is associated with the bed map information and is of a patient selected for each learner, in the storage unit with the simulated patient information associated with leaner information of the learner;

processing for displaying the bed map information associated with the learner information on the administrator terminal, when an arbitrary simulated patient is selected from the displayed bed map information, displaying an electronic health record relevant to the selected simulated patient on the administrator terminal, and when receiving a request for transition to an editing mode from the administrator terminal, displaying the electronic health record such that the electronic health record can be edited; and processing for displaying, based on the display condition, the bed map information associated with the learner information on the learner terminal such that the bed map information cannot be edited and, when an arbitrary simulated patient is selected from the displayed bed map information, displaying an electronic health record relevant to the selected simulated patient on the learner terminal such that the electronic health record cannot be edited.

5. The educational electronic health record program according to claim 4, wherein the simulated patient information stored in the storage unit is associated with information included in the simulated patient information and includes virtually set date and time information, and the program causes the educational electronic health record server to further execute:

processing for setting a date and time different from a date and time included in the date and time information; and processing for generating the patient health record information displayed on the learner terminal, based on the set date and time.

6. The educational electronic health record program according to claim 4, wherein the program causes the educational electronic health record server to further execute processing for updating the simulated patient information stored in the storage unit, based on edited new patient health record information.

\* \* \* \* \*